(12) United States Patent
Wesjohann et al.

(10) Patent No.: US 9,913,904 B2
(45) Date of Patent: Mar. 13, 2018

(54) USE OF AN AGENT CONSISTING OF ANTIBODIES AND/OR INSULIN-LIKE GROWTH FACTOR ANTAGONISTS

(71) Applicants: MAT-MALTA ADVANCED TECHNOLOGIES LIMITED, St. Julians (MT); FREISTAAT BAYERN REPRESENTED BY JULIUS-MAXIMILIANS-UNIVERSITÄT WÜRZBURG, Würzburg (DE)

(72) Inventors: Jan Wesjohann, Visbek (DE); Günter Sprotte, Pentling-Grasslfing (DE); Ana Maria Waaga-Gasser, Würzburg (DE)

(73) Assignee: IGNOVA GMBH, Oberursel (DE)

(*) Notice: Subject to any disclaimer, the term of this patent is extended or adjusted under 35 U.S.C. 154(b) by 0 days.

(21) Appl. No.: 15/433,497

(22) Filed: Feb. 15, 2017

(65) Prior Publication Data
US 2017/0252438 A1 Sep. 7, 2017

Related U.S. Application Data

(62) Division of application No. 14/110,104, filed as application No. PCT/EP2012/055485 on Mar. 28, 2012, now Pat. No. 9,801,938.

(30) Foreign Application Priority Data

Apr. 5, 2011 (DE) .......... 10 2011 006 809

(51) Int. Cl.
| | |
|---|---|
| C07K 16/02 | (2006.01) |
| A61K 39/40 | (2006.01) |
| C07K 16/12 | (2006.01) |
| C07K 16/14 | (2006.01) |
| A61K 39/00 | (2006.01) |

(52) U.S. Cl.
CPC .......... *A61K 39/40* (2013.01); *C07K 16/1203* (2013.01); *C07K 16/1232* (2013.01); *C07K 16/1235* (2013.01); *C07K 16/1275* (2013.01); *C07K 16/1282* (2013.01); *C07K 16/14* (2013.01); *A61K 2039/507* (2013.01); *C07K 2317/11* (2013.01); *C07K 2317/23* (2013.01)

(58) Field of Classification Search
None
See application file for complete search history.

(56) References Cited

U.S. PATENT DOCUMENTS

| | | |
|---|---|---|
| 2001/0055595 A1 | 12/2001 | Goldenberg |
| 2003/0099633 A1 | 5/2003 | Campbell et al. |
| 2006/0034846 A1 | 2/2006 | Ezban et al. |
| 2007/0122413 A1 | 5/2007 | Sivakumar et al. |
| 2007/0207187 A1 | 9/2007 | Yajima |
| 2011/0200591 A1 | 8/2011 | Bisgaard-Frantzen |
| 2013/0273074 A1 | 10/2013 | Rawlin |
| 2014/0099328 A1 | 4/2014 | Wesjohann |
| 2014/0112937 A1 | 4/2014 | Wesjohann |

FOREIGN PATENT DOCUMENTS

| | | |
|---|---|---|
| EP | 0225254 A2 | 6/1987 |
| EP | 0 955 061 A1 | 11/1999 |
| EP | 1125585 A1 | 8/2001 |
| EP | 1982999 A1 | 10/2008 |
| WO | WO-92/16624 A1 | 10/1992 |
| WO | WO-9625155 A1 | 8/1996 |
| WO | WO-0130300 A2 | 5/2001 |
| WO | WO-01/48018 A1 | 7/2001 |
| WO | WO-200202641 A1 | 1/2002 |
| WO | WO-2004078209 A1 | 9/2004 |
| WO | WO-2008025099 A1 | 3/2008 |
| WO | WO-2008067234 A2 | 6/2008 |
| WO | WO-2008073463 A2 | 6/2008 |
| WO | WO-2009077993 A2 | 6/2009 |
| WO | WO-2009113065 A1 | 9/2009 |
| WO | WO-2009151717 A2 | 12/2009 |
| WO | WO-2010/125565 A2 | 11/2010 |
| WO | WO-2011036539 A1 | 3/2011 |
| WO | WO-2012023051 A2 | 2/2012 |
| WO | WO-2012136534 A2 | 10/2012 |
| WO | WO-2013009843 A1 | 1/2013 |

OTHER PUBLICATIONS

XP009186578—Elvira Scheckies, "Polyclonal Antibodies—An Introduction into the Theory and Practice of Antibody Production," VCH Verlagsgesellschaft, 1996, pp. 2-7, English Translation.
MacCallum et al., "Antibody-antigen Interactions: Contact Anaylsis and Binding Site Topography", J. Mol. Biol., (1996) 262, pp. 732-745.
Colman P.M., "Effects of amino acid sequence changes on antibody-antigen interactions", Research in Immunology, 145, pp. 33-36, 1994.
Poxton, I.R., "Antibodies to lipopolysaccharide," Journal of Immunological Methods, 186 (1995), pp. 1-15.
Rudikoff, et al., "Single amino acid substitution altering antigen-binding specificity", Proc. Natl. Acad. Sci USA vol. 79, pp. 1979-1983, Mar. 1982.
William E. Paul, Fundamental Immunology, 3rd Edition, 1993, pp. 292-295.
Kawagashira Y et al: Differential response to intravenous immunoglobulin (IVIg) therapy among multi focal and polyneuropathy types of painful diabetic neuropathy, Journal of Clinical Neuroscience, vol. 17, No. 8, 2010, p. 1003-1008, XP027129028.
Cats E A et al: "New liquid intravenous immunoglobulin (10 % IVIg) for treatment of multifocal motor neuropathy; A prospective study of efficacy, safety and tolerability", Journal of Neurology, vol. 255, No. 10, 2008, p. 1598-1599, XP019657652.
Schade R et al: "Chicken Egg Yolk Antibodies (Igy-technology): A Review of Progress in Production and Use in Research and Human and Veterinary Medicine", Alternatives to Laboratory Animals (ATLA.), vol. 33, No. 2, 2005, p. 129-154, XP009057556.

(Continued)

*Primary Examiner* — Brian Gangle
(74) *Attorney, Agent, or Firm* — Polsinelli PC

(57) ABSTRACT

The present invention relates to the use of a composition selected from the group consisting of antibodies, antibody fragments, insulin-like growth factor antagonists, Toll-like receptor antagonists and mixtures thereof for the treatment or the prophylaxis of certain diseases.

12 Claims, 9 Drawing Sheets

(56) References Cited

OTHER PUBLICATIONS

Waaga-Gasser A.M. et al: "Oral immunoglobulin induces mononuclear cell apoptosis in patients suffering from idiopathic chronic pain syndrome: Results from a pilot study", International Journal of Clinical Pharmacology and Therapeutics, vol. 47, No. 7, 2009, p. 421-433, XP009150941.

Struff W G et al: "Bovine colostrum as a biologic in clinical medicine: A review—Part II: Clinical Studies", International Journal of Clinical Pharmacology and Therapeutics, vol. 46, No. 5, 2008, p. 211-225, XP009150270.

Horikoshi Toshio et al: "IgG Antibody from Hen Egg Yolks: Purification by Ethanol Fractionation", Journal of Food Science, vol. 58, No. 4, 1993, p. 739-742, 779, XP002678305.

Akita E.M. et al: "Comparison of four purification methods for the production of immunoglobulins from eggs laid by hens immunized with an enterotoxigenic *E. coli* strain", Journal of Immunological Methods, vol. 160, No. 2, 1993, p. 207-214, XP023974043.

Bizhanov G et al: "A novel method, based on lithium sulfate precipitation for purification of chicken egg yolk immunoglobulin Y, applied to immunospecific antibodies against Sendai virus.", Scandinavian Journal of Laboratory Animal Science, vol. 31, No. 3, Jan. 1, 2004, p. 121-130, XP002589471.

Yokoyama H et al: "Passive Protective Effect of Chicken Egg Yolk Immunoglobulins against Experimental Enterotoxigenic *Escherichia coli* Infection in Neonatal Piglets", Infection and Immunity, vol. 60, No. 3, Mar. 1992, p. 998-1007, XP002109373.

Yokoyama H et al: "A Two-Step Procedure for Purification of Hen Egg Yolk Immunoglobulin G: Utilization of Hydroxypropylmethylcellulose Phtalate and Synthetic Affinity Ligand Gel (Avid AL®)", Poultry Science, vol. 72, 1993, p. 275-281, XP008091830.

Yokoyama H et al: "Oral passive immunization against experimental salmonellosis in mice using chicken egg yolk antibodies specific for *Salmonella enteritidis* and *S. typhimurium*", Vaccine, vol. 16, No. 4, 1998, p. 388-393, XP004099299.

Yokoyama H et al: "Effect of Oral Egg Antibody in Experimental F18+*Escherichia coli* Infection in Weaned Pigs", The Journal of Veterinary Medical Science, vol. 59, No. 10, Oct. 1997, p. 917-921, XP002678452.

Yokoyama K et al: "Effects of egg yolk antibody against *Porphyromonas* gingivalis gingipains in periodontitis patients", Journal of Oral Science, vol. 49, No. 3, 2007 p. 201-206, XP002678729.

Javier Hernandez-Campos F et al: "Purification of Egg Yolk Immunoglobulin (IgY) by Ultrafiltration: Effect of pH, Ionic Strength, and Membrane Properties", Journal of Agricultural and Food Chemistry, vol. 58, No. 1, Jan. 2010, p. 187-193, XP002678453.

Suzuki H et al: "*Effect of dietary anti-Helicobacter pylori-urease immunoglobulin Y on Helicobacter pylori infection*", Alimentary Pharmacology & Therapeutics, vol. 20, (Supp. 1), Jul. 2004, p. 185-192, XP002678730.

Jennifer Kovacs and Yoshinori Mine. 2005. "Microencapsulation for the gastric and intestinal passage controlled release of immunoglobulin Y". Journal of Immunological Methods. vol. 296 pp. 199-209.

Sprotte et al. (translation of EP0781560, published Jul. 2, 1997).

USE OF AN AGENT CONSISTING OF ANTIBODIES AND/OR INSULIN-LIKE GROWTH FACTOR ANTAGONISTS

TECHNICAL FIELD

The present invention relates to the use of an agent selected from the group consisting of antibodies, antibody fragments, insulin-like growth factor antagonists, Toll-like receptor antagonists and mixtures thereof for the treatment or the prophylaxis of certain diseases.

Diseases of the human body are currently treated with an abundance of therapeutic agents. Similarly, a large number of agents are employed for the prophylaxis of diseases. In spite of this large number of treatment options, there is a permanent need for novel therapy and prophylaxis agents, for the development of novel therapy methods and for the improvement and further development of known therapy methods.

For certain diseases (e.g. chronic pain syndromes), it has hitherto been known from the state of the art that antibodies against endotoxins can be employed in their treatment. Endotoxins are decomposition products of bacteria, which can trigger numerous physiological reactions in humans. Antibodies against endotoxins are also contained in the natural antibody spectrum of bovine colostrum.

The oral use of immunoglobulins from plasma, colostral milk, milk, eggs or cell cultures for the treatment and prophylaxis of chronic states of pain without physiological correlation is disclosed in the state of the art (DE 195 48 221 C1).

W. G. Struff and G. Sprotte, Int. J. Clin. Pharmacol. Ther., 2007 April; 45(4):193-202 disclose biotechnological standards, pharmacodynamic and pharmacokinetic characteristics and treatment methods of bovine colostrum.

W. G. Struff and G. Sprotte, Int. J. Clin. Pharmacol. Ther., 2008 May; 46(5):211-25 disclose clinical studies with bovine colostrum.

A. M. Waaga-Gasser et al., Int. J. Clin. Pharmacol. Ther., 2009 July; 47(7):421-33 disclose the treatment of patients suffering from chronic pain syndrome with oral immunoglobulin from bovine colostrum.

A. Goebel et al. disclose data which show an increased permeability in the gastroduodenal region and in the small intestine in the presence of two chronic pain syndromes (fibromyalgia and complex regional pain syndrome).

The object of the present invention was thus to provide agents which positively influence, in particular improve the prophylaxis and/or therapy of certain diseases. The certain diseases in this context are diseases selected from group X consisting of:

polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))

arthrosis other than osteoarthrosis; in particular activated arthrosis, primary arthrosis, secondary arthrosis enthesiopathies in collagenoses lateral epicondylitis achillodynia calcaneodynia and heel spur periarthritis humero-scapularis Tietze's syndrome (sternoclavicular joint arthropathy)

arthropathy of the iliosacral joint myoarthropathy of the masticatory apparatus, craniomandibular dysfunction cervical spine syndrome after deceleration trauma diverticulitis in colonic diverticulosis neurodermatitis asthma interstitial cystitis (painful bladder syndrome)

food allergy allergy to light, in particular polymorphic photodermatosis mucositis, in particular oral mucositis and/or mucositis after radiation therapy (radiogenic mucositis) and/or mucositis after and/or under chemotherapy mucosal ulcers in Behcet's syndrome mucosal erosions in pemphigus vulgaris mucosal lesions in scleroderma mucosal lesions in Sjörgen's syndrome migraine without aura cardiovascular diseases.

A further (part) object of the present invention was to provide compositions which influence, in particular improve the treatment or the prophylaxis of a disease selected from group Y as described below, and in particular the diseases irritable bowel syndrome reactive arthritis ulcerative colitis Crohn's disease graft-versus-host disease.

The present objects are achieved by the subject matter of the independent claims.

SUMMARY OF THE INVENTION

A first embodiment of the present invention accordingly relates to an agent selected from the group consisting of antibodies, antibody fragments, insulin-like growth factor antagonists, Toll-like receptor antagonists and mixtures thereof for the treatment or the prophylaxis of a disease having anatomically pathological correlations, selected from group X consisting of polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))

arthrosis other than osteoarthrosis; in particular activated arthrosis, primary arthrosis, secondary arthrosis enthesiopathies in collagenoses lateral epicondylitis achillodynia calcaneodynia and heel spur periarthritis humero-scapularis Tietze's syndrome (sternoclavicular joint arthropathy)

arthropathy of the iliosacral joint myoarthropathy of the masticatory apparatus, craniomandibular dysfunction cervical spine syndrome after deceleration trauma diverticulitis in colonic diverticulosis neurodermatitis asthma interstitial cystitis (painful bladder syndrome)
food allergy
allergy to light, in particular polymorphic photodermatosis
mucositis, in particular oral mucositis and/or mucositis after radiation therapy (radiogenic mucositis) and/or mucositis after and/or under chemotherapy
mucosal ulcers in Behcet's syndrome
mucosal erosions in pemphigus vulgaris
mucosal lesions in scleroderma
mucosal lesions in Sjörgen's syndrome
migraine without aura
cardiovascular diseases
where in the case of asthma in the case where the agent comprises neither an insulin-like growth factor antagonist nor a Toll-like receptor antagonist
  (i.) the treatment or prophylaxis is carried out orally and/or
  (ii.) the antibodies and/or antibody fragments target Gram-negative bacteria to the extent of at least 5 wt. %, preferably 10 wt. %, based on the total antibody content of the agent.

A further embodiment of the present invention relates to an agent selected from the group consisting of antibodies, antibody fragments, insulin-like growth factor antagonists, Toll-like receptor antagonists and mixtures thereof for promotion of the apoptosis of monocytes which have taken up lipopolysaccharides, in the treatment or for the prophylaxis of a disease selected from groups X and Y consisting of
  polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions
  peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))
  arthrosis other than osteoarthrosis; in particular activated arthrosis, primary arthrosis, secondary arthrosis
  enthesiopathies in collagenoses
  lateral epicondylitis
  achillodynia
  calcaneodynia and heel spur
  periarthritis humero-scapularis
  Tietze's syndrome (sternoclavicular joint arthropathy)
  arthropathy of the iliosacral joint
  myoarthropathy of the masticatory apparatus, craniomandibular dysfunction
  cervical spine syndrome after deceleration trauma
  diverticulitis in colonic diverticulosis
  neurodermatitis
  asthma
  interstitial cystitis (painful bladder syndrome)
  food allergy
  allergy to light, in particular polymorphic photodermatosis
  mucositis, in particular oral mucositis and/or mucositis after radiation therapy (radiogenic mucositis) and/or mucositis after and/or under chemotherapy
  mucosal ulcers in Behcet's syndrome
  mucosal erosions in pemphigus vulgaris
  mucosal lesions in scleroderma
  mucosal lesions in Sjörgen's syndrome
  migraine without aura
  cardiovascular diseases
  irritable bowel syndrome
  reactive arthritis
  ulcerative colitis
  Crohn's disease
  graft-versus-host disease.

DETAILED DESCRIPTION OF THE INVENTION

Figure 1:
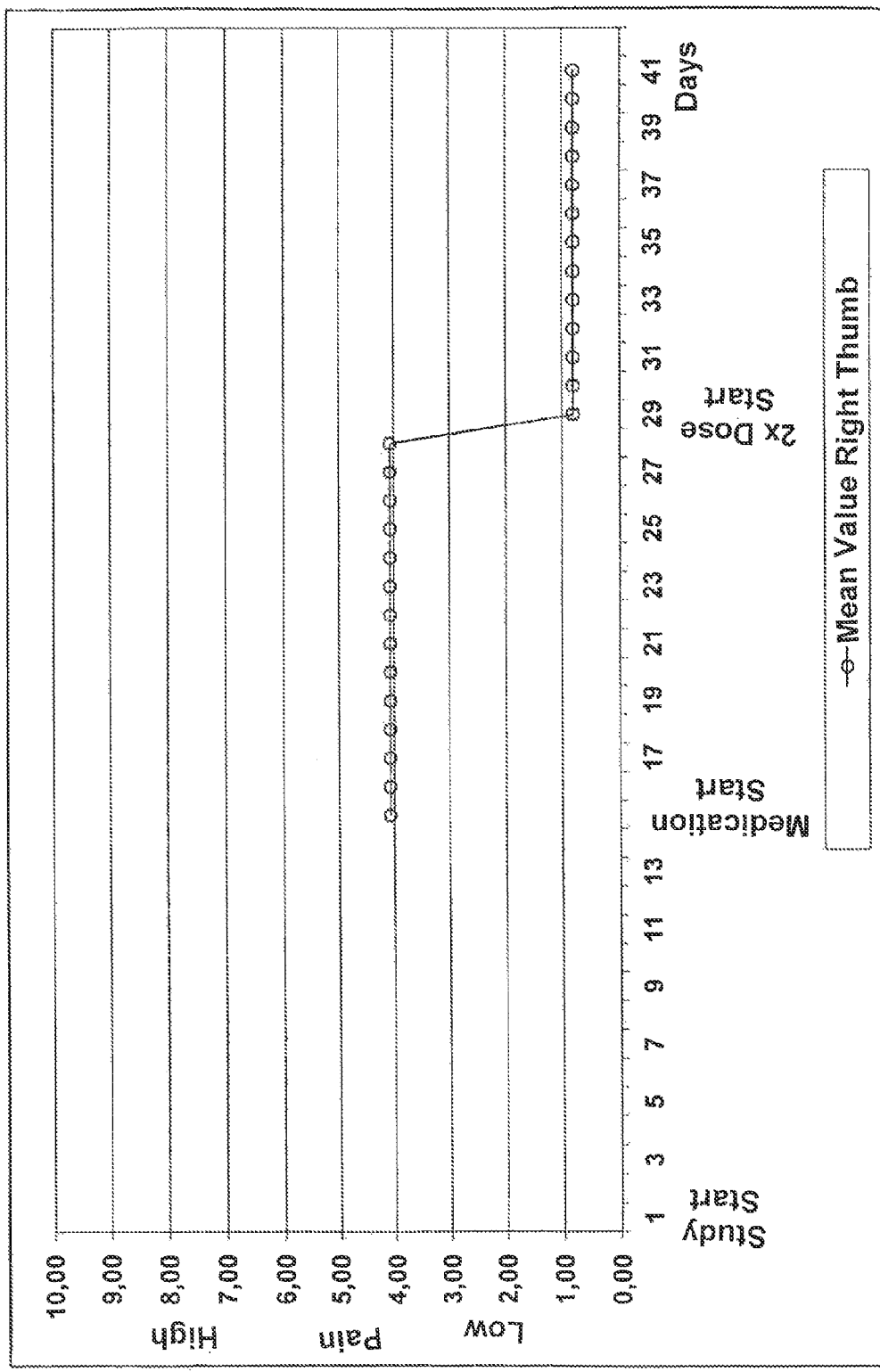
FIG. 1 is a graphical representation of the pain level as the mean values of the numerical daily ratings for two study periods.

In studies conducted by ourselves, it has been found, surprisingly, that the diseases mentioned can be influenced by a common mechanism.

The studies have furthermore shown, surprisingly, that the diseases mentioned can be caused and prolonged at least partially by a defective biological barrier against bacterial toxins, in particular endotoxins. In addition to the defective mechanical barrier function of the mucous membranes of the digestive tract (Goebel A. et al., Rheumatology, 2008), defective processing by immune cells of the toxins recognized as an antigen (Waaga-Gasser A. M. et al, International Journal of Clinical Pharmacology and Therapeutics, 2009) may furthermore also be mentioned as a further prerequisite for the development of disease symptoms of the diseases mentioned. However, the fact that these mechanisms also apply to the diseases of groups X and Y was not to be expected against the background of the state of the art.

Defective processing of bacterial antigens consists of "organized cell death", i.e. apoptosis, not being started to a sufficient extent in the immune cells of the mucous membranes which take up the antigen (in particular in the monocytes). Apoptosis usually leads to local neutralization of the toxins within the immune barrier of the digestive tract.

In patients with a defective mechanical and immunological barrier function, there is an excess of immune cells in venous blood which continue to present bacterial toxins from the digestive tract compared with patients with an intact barrier function. These immune cells have not entered into apoptosis after taking up the toxin—as would usually be expected. In close correlation with this finding in the cell immune system, a constellation of a defective humoral immune response typical of this disease mechanism is found in the serum or plasma of the patient.

Surprisingly, it has now been possible to demonstrate in the studies conducted a therapeutic and/or prophylactic effect in the use of an agent comprising antibodies, antibody fragments, insulin-like growth factor antagonists and/or Toll-like receptor antagonists in patients suffering from one or more of the diseases listed. In addition to an idiopathic pain syndrome, the patients in the studies predominantly suffered from one or more of the diseases listed (co-morbidities).

The results of the clinical studies conducted with the use of an agent according to one embodiment of this invention show for the first time healing actions on co-morbidities of these study patients. It has moreover been demonstrated for the first time, and surprisingly, that endotoxins can play a pathogenic role not only in the triggering and maintenance of chronic (hitherto idiopathic) pain syndromes, but also in the typical symptoms of known diseases.

One embodiment according to the invention of the present invention is an agent selected from the group consisting of antibodies, antibody fragments, insulin-like growth factor antagonists, Toll-like receptor antagonists and mixtures thereof for the treatment or the prophylaxis of a disease selected from groups X consisting of polyneuropathy, mononeuropathy (possibly without trigeminal neuralgia), autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))

arthrosis other than osteoarthrosis; in particular activated arthrosis, primary arthrosis, secondary arthrosis enthesiopathies in collagenoses achillodynia calcaneodynia and heel spur periarthritis humero-scapularis Tietze's syndrome (sternoclavicular joint arthropathy)

arthropathy of the iliosacral joint myoarthropathy of the masticatory apparatus, craniomandibular dysfunction cervical spine syndrome after deceleration trauma diverticulitis in colonic diverticulosis neurodermatitis asthma interstitial cystitis (painful bladder syndrome)

food allergy allergy to light, in particular polymorphic photodermatosis mucositis, in particular oral mucositis and/or mucositis after radiation therapy (radiogenic mucositis) and/or mucositis after and/or under chemotherapy mucosal ulcers in Behcet's syndrome mucosal erosions in pemphigus vulgaris mucosal lesions in scleroderma mucosal lesions in Sjörgen's syndrome migraine without aura cardiovascular diseases where in the case of asthma in the case where the agent comprises neither an insulin-like growth factor antagonist nor a Toll-like receptor antagonist 1. the treatment or prophylaxis is carried out orally and/or
2. the antibodies and/or antibody fragments target Gram-negative bacteria to the extent of at least 5 wt. %, preferably 10 wt. %, based on the total antibody content of the agent.

For further or all of the abovementioned indications, it may also be preferable for the agent to be employed according to the invention to comprise neither an insulin-like growth factor antagonist nor a Toll-like receptor antagonist.

In the context of the present invention an antibody or antibody fragment is a protein from the class of globulins having at least one specific antigen-binding site (paratope). Antibodies are formed in vivo as a reaction to particular antigens.

Substances which, after introduction into the organism of humans and animals, cause a specific immune response which manifests itself inter alia in the formation of antibodies are called antigens.

An antigen can have several epitopes (antigen determinant, antigen-binding site) to which different antibodies in each case can bind. For this reason in vivo the formation of a mixture of antibodies of different specificity (polyclonal antibodies) always occurs, even if immunization has been carried out with a single antigen. Conversely, antibodies of a single mono- or bispecificity are referred to as monoclonal antibodies.

A particular antigen as a rule induces the formation of only a few, quite particular matching antibodies, which usually recognize only this foreign substance via specific, non-covalent binding.

Antigens in the context of the present text are, in particular, microorganisms (species) or parts thereof.

In the context of this text, the indications described above are to be understood as meaning diseases having an anatomically pathological correlation. Anatomically pathological correlation here means that in particular a detectable tissue damage is regarded as the cause of the particular disease symptoms. Such a tissue damage can also be an inflammation and/or be caused by pathological metabolic states. It is pointed out that the above definition of anatomically pathological correlation expressly does not also include the physiological situation of the action mechanism found and described here, namely the presence of toxin-loaded monocytes. This knowledge has not existed in the state of the art and was therefore not known as an anatomically pathological correlation.

Surprisingly, a therapeutic and/or prophylactic effect exists in the use according to the invention of an agent selected from the group consisting of antibodies, antibody fragments, insulin-like growth factor antagonists and/or Toll-like receptor antagonists in patients suffering from one or more of the diseases listed in group X and/or group Y.

The use according to one embodiment according to the invention shows further advantages: the use according to the invention has a lower potential for side effects than conventional therapeutic approaches, but the use according to the invention is highly effective.

A further positive effect which is found in a use according to one embodiment according to the invention is the improvement in the quality of sleep and mood in patients affected. It has furthermore been found that antibodies can often also assist healing processes.

The reactive arthritis mentioned in group Y relates to inflammatory diseases of individual large joints (monoarthritis) or of vertebral joints (spondylarthritis/spondylarthropathy) following bacterial infections of the digestive tract or of the urethra. These are "indirect" consequences of infections in which the pathogens themselves do not lead to inflammation of the joint, but bacterial antigens enter into the joint affected by translocation in the bloodstream from the site of the infection and trigger the inflammation "reactively" there.

The use according to the invention/the agent according to the invention has been found to be particularly patient-friendly in an oral treatment and/or prophylaxis.

A preferred embodiment according to the invention thus relates to an agent according to the invention, preferably according to the preceding embodiment, characterized in that it is suitable for carrying out the treatment or the prophylaxis orally.

Following oral intake, the agent used or the antibodies and/or antibody fragments bind their specific antigens (and also toxins) on their passage through the digestive tract and also arrive at or in the mucous membranes having a defective barrier function, where they impart to the immune cells which have already taken up endotoxins there the antibody- or antigen-specific biological signal for apoptosis. Imparting of the apoptosis signal is also attributed to the insulin-like growth factor antagonists which can be employed alternatively or additionally.

Oral (enteral) therapy has various advantages over parenteral administration forms (e.g. intravenous, intramuscular, subcutaneous): an oral administration in the context of a use according to the invention is associated with a considerably lower potential for side effects for the patient, since the agent used (or the antibodies and/or antibody fragments) do not enter into the blood circulation. It is in fact digested like other (food) proteins in the course of the gastrointestinal passage, before it enters into the organism in the form of simple amino acids. Parenterally administered proteins (e.g. from blood plasma or serum), on the other hand, are subject to the control of the immune system with respect to tolerance or defence. Only human plasma or serum proteins are tolerated parenterally with an acceptable risk of side effects. Oral use, on the other hand, is subject to the natural tolerance of proteins in the digestive tract and also renders possible the use of xenogeneic antibodies, which seems desirable above all from economic aspects. Furthermore, this oral therapeutic form is also pleasanter and more convenient for the patient. No (e.g. venous) access is necessary for administration. Compared with other forms of administration, an improved compliance by the patient and associated with this an increased potential for onset of action is to be expected.

A particularly preferred agent according to the invention, preferably according to one of the preceding preferred embodiments, is characterized in that the antibodies and/or antibody fragments at least partially target Gram-negative bacteria. This leads to a significant increase in the action of the agent.

Gram-negative bacteria are preferably selected from the group consisting of *Streptobacillus moniliformis*, meningococcus, *Chlamydophila*, *chlamydia*, spirochetes, cyanobacteria, species of the Proteobacteria phylum, in particular Enterobacteriaceae (*Escherichia coli, Salmonella, Shigella, Klebsiella, Proteus, Enterobacter*), *Pseudomonas* bacteria, *Legionella* bacteria, *Neisseria* bacteria, *Rickettsia* bacteria, *Pasteurella multocida* bacteria and species of the Bacteroidetes strain.

A particularly preferred agent according to the invention, preferably according to one of the preceding embodiments, is characterized in that the antibodies, antibody fragments, insulin-like growth factor antagonists and/or Toll-like receptor antagonists are present at least partially in the form of monoclonal antibodies, polyclonal antibodies, primatized monoclonal antibodies, antibody fusion proteins, antibody fragments, conjugated antibodies, radioactively labelled antibodies, bispecific antibodies and/or monoclonal intrabody antibodies.

A particularly preferred agent according to the invention, preferably according to one of the preceding embodiments, is characterized in that the antibodies, antibody fragments, insulin-like growth factor antagonists and/or Toll-like receptor antagonists are present at least partially in the form of monoclonal antibodies, where the monoclonal antibodies are selected from the group consisting of murine, chimaeric, humanized and human monoclonal antibodies.

Very particularly preferably, in the context of the use according to the invention the antibodies, antibody fragments, insulin-like growth factor antagonists and/or Toll-like receptor antagonists are present at least partially in the form of human monoclonal antibodies. Human monoclonal antibodies have the lowest immunogenicity (property of triggering a reaction of the immune system called an immune response) compared with murine, chimaeric and humanized monoclonal antibodies, where murine monoclonal antibodies cause the highest immunogenicity.

A particularly preferred agent according to the invention, preferably according to one of the preceding embodiments, is characterized in that the agent comprises immunoglobulin A, immunoglobulin D, immunoglobulin E, immunoglobulin M, immunoglobulin G and/or immunoglobulin Y or consists of these.

Very particularly preferably, in the context of a particularly preferred use according to the invention the agent comprises immunoglobulin Y (IgY).

A particularly preferred agent according to the invention, preferably according to one of the preceding embodiments, is characterized in that the antibodies, antibody fragments, insulin-like growth factor antagonists and/or Toll-like receptor antagonists have been obtained at least partially, but preferably completely from birds.

A particularly preferred agent according to the invention, preferably according to one of the preceding embodiments, is characterized in that the antibodies, antibody fragments, insulin-like growth factor antagonists and/or Toll-like receptor antagonists have been obtained at least partially, but preferably completely from chickens.

Agents to be used according to the invention which have been obtained at least partially, but preferably completely from birds, in particular from chickens, offer the advantage inter alia of a surprisingly high tolerability when administered to humans and/or animals. In addition, these agents which are preferably to be used according to the invention can be prepared in a high purity (agent concentration), so that in therapeutic use the dosage quantities actually to be employed (agent plus further constituents) can be kept relatively low. As a result, the burden to the patient associated with intake of the agent is lowered. Furthermore, antibodies obtained from birds, here in particular chickens, can be prepared in an economically favourable manner, also because correspondingly large animal populations exist.

A particularly preferred agent according to the invention, preferably according to one of the preceding preferred embodiments, is characterized in that the antibodies, antibody fragments, insulin-like growth factor antagonists and/or Toll-like receptor antagonists are present at least partially in the form of monoclonal antibodies, polyclonal antibodies, primatized monoclonal antibodies, antibody fusion proteins, antibody fragments, conjugated antibodies, radioactively labelled antibodies, bispecific antibodies and/or monoclonal intrabody antibodies, and in that the antibodies, antibody fragments, insulin-like growth factor antagonists and/or Toll-like receptor antagonists have been obtained at least partially, preferably completely from chickens.

In our own studies it has been found, surprisingly, that particularly good results were achieved when using the agent according to the invention if the antibodies, antibody fragments, insulin-like growth factor antagonists and/or Toll-like receptor antagonists were obtained at least partially from chickens. A surprisingly great improvement in tolerability thus existed in patients compared with agents according to the invention which are to be used from mammals, here in particular cattle.

A particularly preferred agent according to the invention, preferably according to one of the preferred preceding embodiments, is characterized in that the antibodies, antibody fragments, insulin-like growth factor antagonists and/or Toll-like receptor antagonists have been obtained at least partially from liquid and/or dried egg yolk.

A further particularly preferred agent according to the invention, preferably according to one of the preceding embodiments, is characterized in that the antibodies, antibody fragments, insulin-like growth factor antagonists and/or Toll-like receptor antagonists have been obtained at least partially from solid egg yolk powder, preferably from dried defatted egg yolk powder.

Defatted egg yolk powder is obtained by standard processes (removal of fat from dried egg yolk powder), preferably using hexane. After the removal of fat, the defatted egg yolk powder is dried again.

A very particularly preferred agent according to the invention, preferably according to one of the preceding embodiments, is characterized in that the antibodies, antibody fragments, insulin-like growth factor antagonists and/or Toll-like receptor antagonists have been obtained at least partially from dried, defatted egg yolk powder, where the defatted egg yolk powder has been obtained from chicken's eggs.

In the studies we conducted ourselves, surprisingly, the extended antibody spectrum from natural biological sources, in particular from egg yolk, proved to be particularly active. The origin of the agents to be used according to the invention is regularly to be detected from co-substances accompanying the agent. Thus, the agents obtained from egg yolk typically comprise, for example, lipoproteins, such as HDL and LDL, and the water-soluble proteins of the egg yolk, $\alpha$-livetin (80 kDa), $\beta$-livetin (45 kDa) and/or $\gamma$-livetin (150 kDa, which also comprise most of the enzymes found in the egg (Ternes, Acker and Scholtyssek, Ei and Eiprodukte, 1994).

A particularly preferred agent according to the invention, preferably according to one of the preceding embodiments, is characterized in that the agent is a medicament or a constituent of a medicament and/or a constituent of a formulation prepared for administration.

A very particularly preferred agent according to the invention, preferably according to one of the preceding embodiments, is characterized in that the agent is a medicament or a constituent of a medicament and/or a constituent of a formulation prepared for administration, where (preferably bovine) colostrum is used.

In the context of the present invention, the first milk for mammals produced by the female mammary gland to provide optimum nutrition for the newborn in the first days is called bovine colostrum. It is also called pre-milk, colostral milk or beastings (in cows) and comprises proteins, enzymes, vitamins, minerals, growth factors, amino acids and antibodies.

Medicaments or equally medical preparations in the context of this invention are substances or substance compositions which are intended as agents having properties for healing or for prevention of human or animal diseases or can be used in or on the human or animal body or administered to a human or animal in order either to re-establish, to correct or to influence the human or animal physiological functions by a pharmacological, immunological or metabolic action or to establish a medical diagnosis. Preferably, in the context of this text "medicament" is to be understood as meaning a corresponding substance and/or a corresponding substance mixture for which approval exists according to the medical preparations law of the particular country of use, particularly preferably approval according to German medical preparations law. The preferred medicaments in the context of this application text also include so-called "orphan medicaments" (orphan drugs) which are subject to a simplified approval procedure and preferably are approved according to European and/or US law.

A preferred agent according to the invention, preferably according to one of the preceding embodiments, is characterized in that the agent is a constituent of a formulation prepared for administration, where the formulation prepared is selected from the group consisting of pharmaceutical preparations, cosmetic preparations, foodstuffs, food supplements, functional food and medicinal products, and feedstuffs, feed supplements and dietary feed supplements for use in animals.

According to the invention, foodstuffs and corresponding newly developed products to which more than only the pure nutritional and flavour value are added on the basis of particular constituents are summarized as "functional food". Synonymously, but partially also as differentiation, the terms nutriceuticals, foodsceuticals and designer foods are used, which likewise represent embodiments of the preparation in the context of the invention.

In our own studies it has been found, surprisingly, that particularly good results are obtained by a use according to the invention, preferably according to one of the preceding embodiments, where the agent is a constituent of a formulation prepared for administration, if the agent contained in the formulation prepared has been obtained at least partially from chickens, preferably from the egg yolk of chickens.

The antibody-containing protein content of egg yolk can be pasteurized, so that the concentration of pathogenic germs can be adequately lowered without a substantial loss of antibody activity in the product. This starting product for the preparation of a formulation (a preparation to be used according to the invention) prepared for administration can be distinguished from the foodstuff egg yolk by analysis of the antibody spectrum, for example by ELISA or neutrality tests.

Such starting products (antibodies from egg products) are conventionally subjected to conventional concentration processes, such as e.g. the usual defatting processes by means of various solvents, such as hexane, ethanol, acetone or carbon dioxide or further processes by means of:

hydroxypropylmethylcellulose (Yokoyama H. et al., A 2-step procedure for purification of chicken egg-yolk immunoglobulin-G-utilization of hydroxypropylmethylcellulose phthalate and synthetic affinity ligand gel, 1993, Poultry Science, 72, pp. 275-281.)

polyethylene glycol, dextran sulfate, xanthan (Akita E. M., Nakai S., Comparison of four purification methods for the production of immunoglobulins from eggs laid by chickens immunized with an enterotoxogenic *E. coli* strain, 1993, Journal of Immunological Methods, 160 (2), pp. 207-214.)

ethanol (Toshio Horikoshi, et al., IgG Antibody from Hen Egg Yolks: Purification by Ethanol, 1993, Fractionation Journal of Food Science 58 (4), 739-742.)

ultrafiltration (Hernandez-Campos F J et al., Purification of Egg Yolk Immunoglobulin (IgY) by Ultrafiltration: Effect of pH, Ionic Strength, and Membrane Properties, Journal of Agricultural and Food Chemistry, 2009 Dec. 8. [Epub ahead of print])

lithium sulfate (Bizhanov G. et al., A novel method, based on lithium sulfate precipitation for purification of chicken egg yolk immunoglobulin Y, applied to immunospecific antibodies against Sendai virus, 2004, Scandinavian Journal of Laboratory Animal Science, 31 (3), pp. 121-130.).

The mixture consequently comprises further co-factors, in addition to the agent to be used according to the invention, which are the basis for the preparation to be used according to the invention. These co-factors can have a positive effect on the action mechanism and/or the tolerability of the preparation to be used according to the invention.

A preferred use according to the invention of the agent according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g.

A very particularly preferred use according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g, where at least 1.5 wt. %, preferably at least 2.0 wt. %, further preferably at least 5.0 wt. % of the formulation prepared for administration is antibodies and/or antibody fragments, based on the total weight of the formulation.

In the case where a formulation of higher concentration with respect to its antibody content is used, it goes without saying for the person skilled in the art to adapt the dosage of the corresponding formulation prepared for administration. In this case, preferred daily doses are 0.1 g-5 g, further preferably 0.1 g-2 g. A higher activity of a formulation can also be achieved by the use of enteric coatings and/or encapsulations. A combination in which a more highly concentrated formulation is used with an enteric coating and/or encapsulation is likewise possible.

A very particularly preferred use according to the invention, preferably according to one of the preceding embodiments, is characterized in that the treatment or the prophylaxis is carried out by a daily dose of a formulation prepared for administration having an enteric coating and/or having an enteric encapsulation of 0.1-5 g, preferably 0.1-2 g.

An enteric coating or an enteric encapsulation offers the advantage that antibodies contained in the formulation prepared for administration are not denatured during passage through the stomach.

A still further preferred use according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g, where at least 1.5 wt. %, preferably at least 2.0 wt. %, further preferably at least 5.0 wt. % of the formulation prepared for administration is antibodies and/or antibody fragments, based on the total weight of the formulation, and where still preferably the content of IgY antibodies and/or IgY antibody fragments is at least 30%, preferably 60%, further preferably 90% and particularly preferably 100%, based on the total antibody content of the formulation prepared for administration.

A preferred use according to the invention, preferably according to one of the preceding preferred embodiments, is characterized in that the treatment or the prophylaxis is carried out by a daily administration for 4-14 weeks, preferably for 8-12 weeks. A 12-week therapy is particularly preferred. For the above dosage information and durations of therapy, particularly good therapeutic effects with a simultaneously surprisingly good tolerability have been found for a large number of patients.

A preferred use according to the invention, preferably according to one of the preceding preferred embodiments, is characterized in that the treatment or the prophylaxis is carried out by a long-term therapy.

A further embodiment according to the invention of the present invention is a) an agent selected from the group consisting of antibodies, antibody fragments, insulin-like growth factor antagonists, Toll-like receptor antagonists and mixtures thereof, or b) a preparation which comprises an agent selected from the group consisting of antibodies, antibody fragments, insulin-like growth factor antagonists, Toll-like receptor antagonists, for the preparation of a medicament for the treatment or the prophylaxis of a disease selected from group X, where in the case of asthma in the case where the agent comprises neither an insulin-like growth factor antagonist nor a Toll-like receptor antagonist 1. the treatment or prophylaxis is carried out orally and/or
2. the antibodies and/or antibody fragments target Gram-negative bacteria to the extent of at least 5 wt. %, preferably 10 wt. %, based on the total antibody content of the agent.

A further embodiment according to the invention of the present invention is an agent selected from the group consisting of antibodies, antibody fragments, insulin-like growth factor antagonists, Toll-like receptor antagonists for promotion of the apoptosis of monocytes which have taken up lipopolysaccharides, in the treatment or for the prophylaxis of a disease selected from groups X and Y consisting of polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))

arthrosis other than osteoarthrosis; in particular activated arthrosis, primary arthrosis, secondary arthrosis enthesiopathies in collagenoses
achillodynia
calcaneodynia and heel spur
periarthritis humero-scapularis
Tietze's syndrome (sternoclavicular joint arthropathy)
arthropathy of the iliosacral joint
myoarthropathy of the masticatory apparatus, craniomandibular dysfunction
cervical spine syndrome after deceleration trauma
diverticulitis in colonic diverticulosis
neurodermatitis
asthma
interstitial cystitis (painful bladder syndrome)
food allergy
allergy to light, in particular polymorphic photodermatosis
mucositis, in particular oral mucositis and/or mucositis after radiation therapy (radiogenic mucositis) and/or mucositis after and/or under chemotherapy
mucosal ulcers in Behcet's syndrome
mucosal erosions in pemphigus vulgaris
mucosal lesions in scleroderma
mucosal lesions in Sjörgen's syndrome
migraine without aura
cardiovascular diseases
irritable bowel syndrome
reactive arthritis
ulcerative colitis
Crohn's disease
graft-versus-host disease.

A particularly preferred formulation prepared for administration for the uses according to the invention is an antibody product comprising n specific antibodies characterized in that
  a) the n specific antibodies each have an antibody content of at least 6/n wt. %, based on the total antibody content of the antibody product, and
  b) 2, 3 or more of the n specific antibodies target lipopolysaccharide-expressing microorganisms and
  c) the total content of the n specific antibodies is 7 wt. %, based on the total antibody content of the antibody product.

Lipopolysaccharides are compounds of fat-like (lipo-) constituents and sugar constituents (polysaccharides). They are contained e.g. in the outer membrane of Gram-negative bacteria and act as antigens. During decomposition of the bacteria, parts of the lipopolysaccharides become free and have a toxic action. These parts are called endotoxins.

Precise information on particularly preferred formulations prepared for administration are to be found in the German patent application with the official application number DE 10 2011 006 781.7, where still further preferred embodiments are also described.

In contrast to agents available to date, which comprise antibodies against endotoxins (e.g. bovine colostrum), such a particularly preferred formulation prepared for administration has a better tolerability.

The invention likewise discloses agents A selected from the group consisting of antibodies, antibody fragments, insulin-like growth factor antagonists, Toll-like receptor antagonists and mixtures thereof for use in the treatment or for the prophylaxis of a disease having an anatomically pathological correlation, selected from the group consisting of
  polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions
  peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))
  arthrosis other than osteoarthrosis; in particular activated arthrosis, primary arthrosis, secondary arthrosis
  enthesiopathies in collagenoses
  achillodynia
  calcaneodynia and heel spur
  periarthritis humero-scapularis
  Tietze's syndrome (sternoclavicular joint arthropathy)
  arthropathy of the iliosacral joint
  myoarthropathy of the masticatory apparatus, craniomandibular dysfunction
  cervical spine syndrome after deceleration trauma
  diverticulitis in colonic diverticulosis
  neurodermatitis
  asthma
  interstitial cystitis (painful bladder syndrome)
  food allergy
  allergy to light, in particular polymorphic photodermatosis
  mucositis, in particular oral mucositis and/or mucositis after radiation therapy (radiogenic mucositis) and/or mucositis after and/or under chemotherapy
  mucosal ulcers in Behcet's syndrome
  mucosal erosions in pemphigus vulgaris
  mucosal lesions in scleroderma
  mucosal lesions in Sjörgen's syndrome
  migraine without aura
  cardiovascular diseases
where in the case of asthma in the case where the agent A comprises neither an insulin-like growth factor antagonist nor a Toll-like receptor antagonist
  1. the treatment or prophylaxis is carried out orally and/or
  2. the antibodies and/or antibody fragments target Gram-negative bacteria to the extent of at least 5 wt. %, preferably 10 wt. %, based on the total antibody content of the agent.

A particularly preferred agent A according to the invention, preferably according to the preceding embodiment, is characterized in that the treatment or the prophylaxis is carried out orally.

A further preferred agent A according to the invention, preferably according to one of the preceding embodiments, is characterized in that the antibodies and/or antibody fragments at least partially target Gram-negative bacteria.

A similarly preferred agent A according to the invention, preferably according to one of the preceding embodiments, is characterized in that the antibodies, antibody fragments, insulin-like growth factor antagonists and/or Toll-like receptor antagonists are present at least partially in the form of monoclonal antibodies, polyclonal antibodies, primatized monoclonal antibodies, antibody fusion proteins, antibody fragments, conjugated antibodies, radioactively labelled antibodies, bispecific antibodies and/or monoclonal intrabody antibodies.

A preferred agent A according to the invention according to the preceding embodiment is characterized in that the monoclonal antibodies are selected from the group consisting of murine, chimaeric, humanized and human monoclonal antibodies.

A further preferred agent A according to the invention, preferably according to one of the preceding embodiments, is characterized in that the agent comprises immunoglobulin A, immunoglobulin D, immunoglobulin E, immunoglobulin M, immunoglobulin G and/or immunoglobulin Y.

A further preferred agent A according to the invention, preferably according to one of the preceding embodiments, is characterized in that the antibodies, antibody fragments, insulin-like growth factor antagonists and/or Toll-like receptor antagonists have been obtained at least partially, but preferably completely from birds.

A further preferred agent A according to the invention, preferably according to one of the preceding embodiments, is characterized in that the antibodies, antibody fragments, insulin-like growth factor antagonists and/or Toll-like receptor antagonists have been obtained at least partially, but preferably completely from chickens.

A similarly preferred agent A according to the invention, preferably according to one of the preceding embodiments, is characterized in that the antibodies, antibody fragments, insulin-like growth factor antagonists and/or Toll-like receptor antagonists have been obtained at least partially, but preferably completely from liquid and/or dried egg yolk.

A very particularly preferred agent A according to the invention, preferably according to one of the preceding embodiments, is characterized in that the antibodies, antibody fragments, insulin-like growth factor antagonists and/or Toll-like receptor antagonists have been obtained at least partially from solid egg yolk powder, preferably from dried defatted egg yolk powder.

A still further preferred agent A according to the invention, preferably according to one of the preceding embodiments, is characterized in that the agent is a medicament or a constituent of a medicament and/or a constituent of a formulation prepared for administration.

A preferred agent A according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g.

A very particularly preferred agent A according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g, where at least 1.5%, preferably at least 2.0%, further preferably at least 5.0% of the formulation prepared for administration is antibodies and/or antibody fragments, based on the total weight of the formulation.

An extremely preferred agent A according to the invention, preferably according to one of the preceding embodiments, is characterized in that the treatment or the prophylaxis is carried out by a daily dose of a formulation prepared for administration of 0.1-10.0 g, preferably 1.0-8.0 g, further preferably of 2.0-7.0 g, where at least 1.5%, preferably at least 2.0%, further preferably at least 5.0% of the formulation prepared for administration is antibodies and/or antibody fragments, based on the total weight of the formulation, and where the content of IgY antibodies and/or IgY antibody fragments is at least 7%, based on the total antibody content of the formulation prepared for administration.

A preferred agent A according to the invention, preferably according to one of the preceding embodiments, is characterized in that the treatment or the prophylaxis is carried out by a daily administration for at least 4 weeks, preferably for at least 8 weeks, particularly preferably for at least 12 weeks.

A preferred agent A according to the invention, preferably according to one of the preceding embodiments, is characterized in that the treatment or the prophylaxis is carried out by a long-term therapy.

The invention likewise discloses
a) agents A selected from the group consisting of antibodies, antibody fragments, insulin-like growth factor antagonists, Toll-like receptor antagonists and mixtures thereof, or
b) preparations which comprise an agent A selected from the group consisting of antibodies, antibody fragments, insulin-like growth factor antagonists, Toll-like receptor antagonists, for the preparation of a medicament for the treatment or the prophylaxis of a disease selected from group X,
where in the case of asthma in the case where the agent A comprises neither an insulin-like growth factor antagonist nor a Toll-like receptor antagonist
1. the treatment or prophylaxis is carried out orally and/or
2. the antibodies and/or antibody fragments target Gram-negative bacteria to the extent of at least 5 wt. %, preferably 10 wt. %, based on the total antibody content of the agent.

All the advantages and embodiments disclosed with respect to the uses according to the invention are applied mutatis mutandis to the agents A according to the invention or formulations for use in the treatment or for the prophylaxis of a disease selected from group X.

The invention likewise discloses agents A selected from the group consisting of antibodies, antibody fragments, insulin-like growth factor antagonists, Toll-like receptor antagonists and mixtures thereof for promotion of the apoptosis of monocytes which have taken up lipopolysaccharides, for use in the treatment or for the prophylaxis of a disease selected from groups X and Y consisting of polyneuropathy, mononeuropathy, autonomic neuropathy, small fibre neuropathy, in each case especially in autoimmune diseases, diabetes mellitus type I and II, diabetes type A, B, C, D, E, F, G, H, polyclonal gammopathy and/or kidney dysfunctions peripheral nerve compression syndromes (such as carpal tunnel syndrome), ulnar nerve entrapment syndrome (cubital tunnel syndrome, Morton's metatarsalgia, Bernhardt-Roth syndrome (meralgia paraesthetica), thoracic outlet syndrome (TOS))

arthrosis other than osteoarthrosis; in particular activated arthrosis, primary arthrosis, secondary arthrosis enthesiopathies in collagenoses lateral epicondylitis achillodynia calcaneodynia and heel spur periarthritis humero-scapularis Tietze's syndrome (sternoclavicular joint arthropathy)

arthropathy of the iliosacral joint myoarthropathy of the masticatory apparatus, craniomandibular dysfunction cervical spine syndrome after deceleration trauma diverticulitis in colonic diverticulosis neurodermatitis asthma interstitial cystitis (painful bladder syndrome)

food allergy allergy to light, in particular polymorphic photodermatosis mucositis, in particular oral mucositis and/or mucositis after radiation therapy (radiogenic mucositis) and/or mucositis after and/or under chemotherapy mucosal ulcers in Behcet's syndrome
mucosal erosions in pemphigus vulgaris
mucosal lesions in scleroderma
mucosal lesions in Sjörgen's syndrome
migraine without aura
cardiovascular diseases
irritable bowel syndrome
reactive arthritis
ulcerative colitis
Crohn's disease
graft-versus-host disease.

All the advantages and embodiments disclosed with respect to the uses according to the invention are applied mutatis mutandis to the agents A according to the invention for use in the treatment or for the prophylaxis of a disease selected from group Y.

The present invention is illustrated in more detail in the following with the aid of examples, where the invention is not limited to the following examples.

Unless stated otherwise, all the (amounts) data here relate to the weight.

EXAMPLES

Preparation Example 1

Precise information on the preparation of the preparation example are to be found in the German patent application having the official application number DE 10 2011 006 781.7 or in PCT/EP2012/055456 (both included via reference). The preparation obtained in accordance with the information there (dried, defatted egg yolk powder) was employed in the following examples. The preparation comprised specific antibodies against the following antigens:
  CA-GTase from *Streptococcus mutans* serotype c from the cells of MT8148
  gingipain from the membrane of *Poryphyromonas gingivalis* (ATCC 33277)
  *Candida albicans* cells (JCM 1542)
  *Escherichia coli* F18 cells, serotype F107 (107/86)
  alpha- and beta-toxin from *Clostridium perfringens* type C (NCTC3227)
  antigen according to H. Yokoyama et al. of the *Salmonella typhimurium* cell (ATCC-13311).

The preparation comprised a total antibody content of approx. 2 wt. %, based on the total weight of the preparation. The total antibody content comprised approx. 10 wt. % of specific antibodies against the antigen types employed (listed above), based on the total antibody content of the preparation. Each specific antibody type (targeting one of the above antigen types employed) was present in the preparation with a content of approx. 10/6 wt. %, based on the total antibody content of the preparation.

Preparation Example 2

Preparation Example 2 was prepared analogously to Preparation Example 1, but the following antigens
  *Escherichia coli* F18 cells, serotype F107 (107/86),
  alpha- and beta-toxin from *Clostridium perfringens* type C (NCTC3227),
  antigen according to H. Yokoyama et al. of the *Salmonella typhimurium* cell (ATCC-13311)
were employed for the immunization.

Preparation Example 2 was moreover used in formulations such as effervescent powders and tablets (in particular enteric tablets). The amount of Preparation Example 2 employed is 0.375 g per tablet or 5 g per pack unit of effervescent powder.

It should be emphasized once more at this point that for the use and the activity of the products according to the invention, the decisive factor is the content of specific antibodies (polyclonal or monoclonal). Since the preparation employed for the following examples is a product which has been obtained from natural sources (eggs from chickens), certain variations in the constituents are of course usual and unavoidable.

Action Example

Neutralization Capacity of the IgY Preparation (Preparation Example 2)

Blood was taken from a healthy volunteer and was then treated with heparin such that it no longer coagulates. Heparin blood results. The heparin blood was then separated into its constituents in order to obtain the blood plasma. 2 ml of the blood plasma obtained in this way were incubated with 2 ml of *E. coli* control standard endotoxin (50 EU/ml) at 37° C. and 5% $CO_2$ for 24 hours. A base plasma solution which comprises a defined amount of a standardized endotoxin is formed. Further notes on the standard endotoxin used can be found in the description of Limulus Amoebocyte Lysate, Endosafe Endochrome-K Test System (US Licence no. 1197).

Provision of the Test Solutions:
  Test solution B: test solution according to the invention against *E. coli, Salmonella* and *C. perfringens* (Preparation Example 2)

In a step a) 100 µl of the base plasma solution prepared were removed and were then mixed homogeneously in a step b) with 100 µl of the dissolved test substance (IgY; 0.25 g/ml, from Preparation Example 2 dissolved in water). The dissolved test substance comprised a mixture of antibodies according to the invention against *E. coli, Salmonella* and *C. perfringens* (Preparation Example 2). In a subsequent step c) the solution prepared in this way was incubated at 37° C. and 5% $CO_2$ for a further 3 hours. In a subsequent step d) the solution was diluted to an endotoxin concentration of 2 EU/ml by addition of water, taking into account the later addition of the LAL reagent, and in a step e) was incubated at 75° C. in a water bath for 5 minutes (inactivation).

The test solution inactivated in this way was then investigated with the aid of the LAL test (Endosafe Endochrome-K Test System). For this, the inactivated test solution was mixed with the LAL reagent, taking into account the method provided by the manufacturer, and the mixture was then pipetted on to a 96-well plate. The investigation was carried out by an ELISA reader and a subsequent evaluation.

Test Solution A: Comparison Solution (Control Solution) which Comprises No Antibodies Test solution A was prepared analogously to test solution B, with the deviation that under step a) 200 µl of base plasma solution were removed and step b) was not carried out.

Test Solution C: Comparison Solution Comprising Antibodies not According to the Invention (IgG, Lactobin N; Dr. Wolz Zell GmbH)

Test solution C was prepared analogously to test solution B, with the deviation that under step b) 100 µl of a Lactobin N solution (manufacturer: Dr. Wolz Zell GmbH) were used. The antibody concentration corresponded to the concentration in test solution B.

Figure 9:
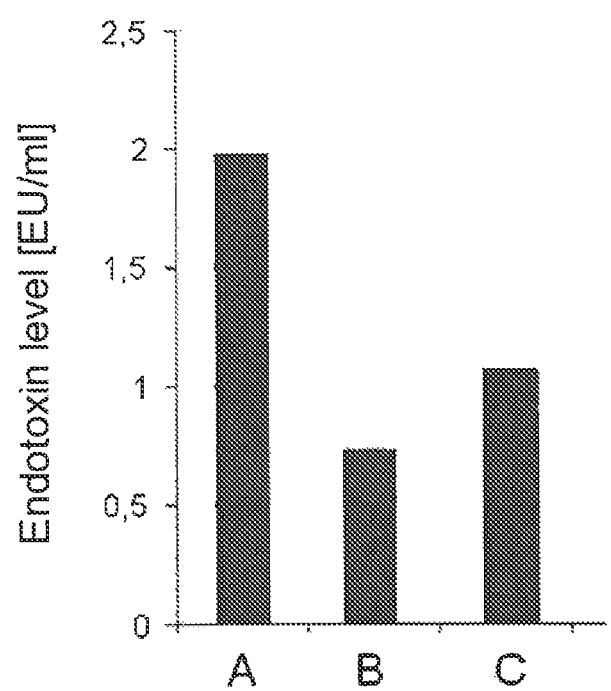
FIG. 9 shows the result of the ELISA test for three test solutions, A, B and C.

FIG. 9 (FIG. 9) shows the result of the ELISA test for test solutions A, B and C. The test quantifies the amount of free endotoxin in the particular test solutions.

Test solution A (control solution), which comprises no antibodies for neutralization of the endotoxins, shows the highest amount of free endotoxin.

Test solution B according to the invention, in contrast, shows the lowest amount.

Compared with test solution C (comparison solution with Lactobin N), test solution B according to the invention shows a significantly better neutralization of the endotoxin than when Lactobin N is used.

USE EXAMPLES

Example 1

Patient data: 32 years old, female
Duration of the pain syndrome: 9 years
Diagnosis:

Complex regional pain syndrome (CRPS type II) after complex injury of the right thumb with fractures of the proximal and distal phalanges and damage to the nerve supply.

After 3 surgical interventions (osteosynthesis of the fracture, removal of metal, surgical correction of deformed extensor tendons) persistent pain at rest and increased during and above all after exercise (painful post-traumatic mononeuropathy).
Local Findings:

Burning stabbing sensations in the whole of the thumb area, more acute at the site of the scars, here also with spontaneous shooting pain and pain triggered by gentle touch (allodynia), and referred pain when pressure applied (Hoffmann-Tinel sign on the damaged skin nerve). In addition, constant throbbing and stinging pain (deep pain) in the two proximal joints of the thumb. Radiographic evidence of arthrosis (pain consistent with activated arthrosis) in these two joints. Compared to the left thumb, the right thumb is significantly narrower, i.e. the skin and soft tissue of the thumb are thinner (atrophy).
Therapeutic Response of the Pain:

No alleviation of pain by centrally and peripherally acting analgesics, antidepressants, anticonvulsives, transcutaneous electrical nerve stimulation.

Opiate injections in the cervical sympathetic trunk of the sympathetic nervous system (GLOA) completely eliminates all pain for an average of 48 hours.
Evidence of a Considerable Improvement in the Disease Symptoms with Oral Therapy with a Hyperimmunoglobulin Against Endotoxin (LPS) from Egg Yolk of Immunized Chickens (Anti-LPS Hyper-IgY):

The patient was included in a therapy study with anti-LPS hyper-IgY. Study period of 4 weeks, divided into two equal time sections of 14 days with a different dosage of the study preparation, testing of the clinical effect (journal documentation of the pain and the parameters of the quality of life) and the effects on a broad spectrum of immunological laboratory parameters before the start and at the end of the study medication.
Therapeutic Effect:

In the first two weeks of the study, daily intake of 2×1.25 g of the preparation (daily dose 2.5 g), including continued elimination of the deep throbbing, pounding pain in the structures near the joint of the right thumb (arthritic pain); neuropathic surface pain in the scar region was unchanged at this dose.

In the second study period, also over a period of two weeks, daily intake of 2×2.5 g of the preparation (daily dose 5 g), resulting also in substantial improvement in neuropathic pain components (see FIG. 1). With the start of freedom from pain and significant recovery in most hand functions, there was also an improvement in concentration ability, range of activity (activity), symptomatic daytime fatigue (chronic fatigue syndrome, physical exhaustion), sleep quality and mood (see FIG. 2).

In the laboratory part of the study, there was a significant reduction of endotoxin-activated monocytes in the peripheral blood (reduction through apoptosis), a decrease in the total number of monocytes to normal values, and quantitative analysis of 22 immuno-messengers (chemokines, cytokines, growth factors) showed a variable but in principle consistent reduction in the plasma concentrations of inflammatory proteins and a significant increase in most anti-inflammatory protein factors.
Withdrawal Attempts:

After completion of the study the trial medication was continued due to a lack of alternatives. Treatment with IgY medication was withdrawn twice, with pain and general symptoms returning after 4-5 days.
Summary:

Neuropathic pain in the injured peripheral nerve region has previously been presented as independent diagnoses of known aetiology and pathogenesis and these characteristics differentiated such pains from idiopathic pain syndromes. Some medicaments are approved for the treatment of painful mono- and polyneuropathies, and there are evidence-based treatment recommendations that include non-medicamentous elements. However, a gross mismatch between the quality of therapeutic effects and the extent of side effects and complications points to significant gaps affecting both patient care and the scientific basis.

The surprisingly positive effect of the specific IgY preparation in this female patient indicates that blood cell-borne endotoxins can, in individual cases, play a causal role in the chronification of pain, even in an injury-induced mononeuropathy.

FIG. 1 is a graphical representation of the pain level as the mean values of the numerical daily ratings for the two study periods.

The ordinate shows the numerical rating scale (NRS). The ordinate has a value ranging from 0 to 10, where "0" means no pain and "10" means the maximum pain imaginable. The abscissa gives the time in days.

Along with the visual analogue scale (VAS), NRS is the most common method of measuring acute and chronic pain so that meaningful conclusions about therapeutic effects can be made based on pain diaries. Patients with chronic pain are familiar with this method of assessing the intensity of their pain.

This patient began keeping the diary records on starting the trial medication on day 15.

Instead of daily values, the mean values over both periods are shown.

Figure 2:
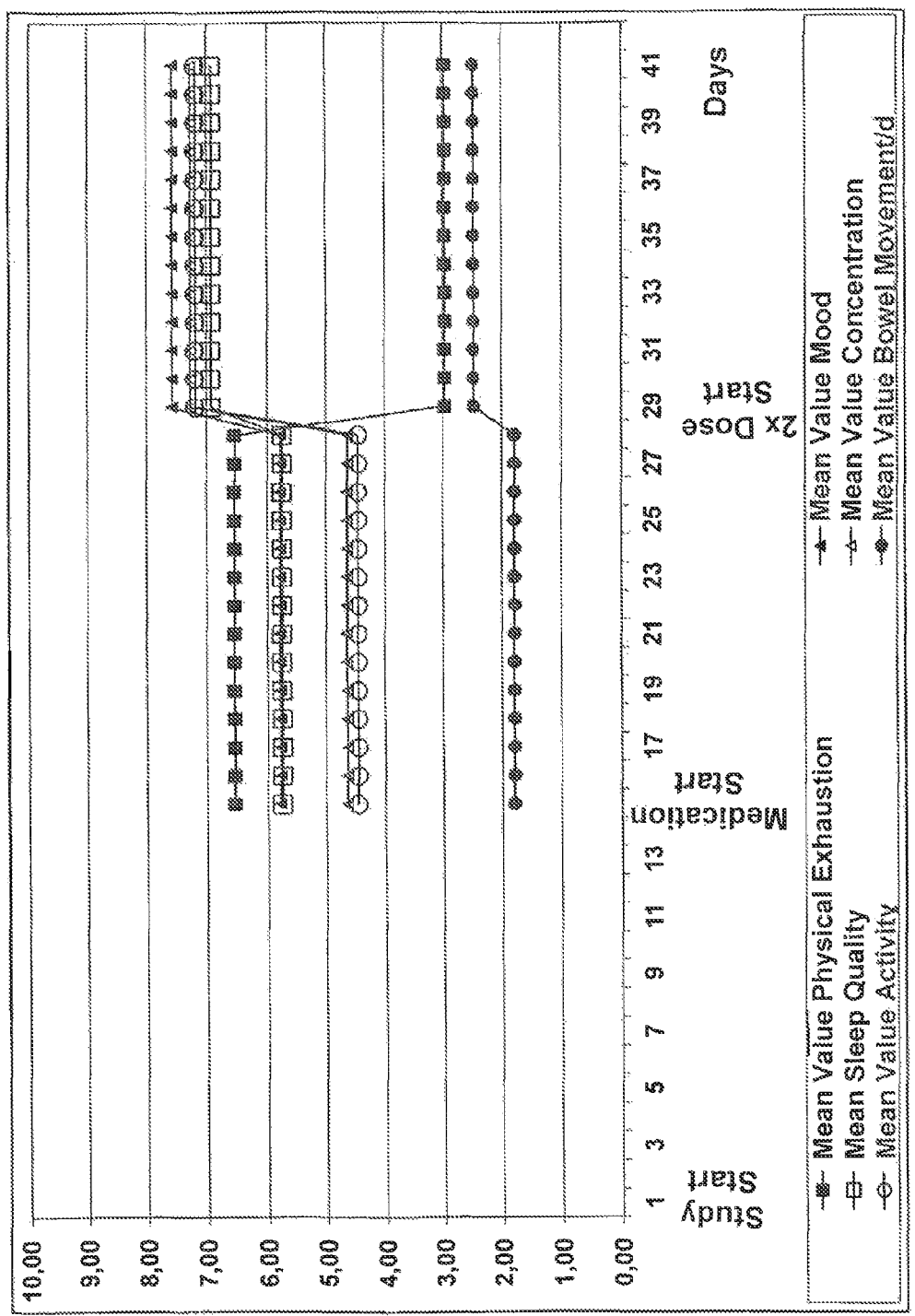
FIG. 2 is a graphical representation of quality of life parameters (physical exhaustion, concentration ability, mood, activity, sleep quality, bowel movement).

FIG. 2 is a graphical representation of quality of life parameters (physical exhaustion, concentration ability, mood, activity, sleep quality, bowel movement).

The positive effects on quality of life parameters are shown particularly clearly by the reduced daytime fatigue and increased range of activity (activity). The numerical rating scale, where 0=no disease symptoms and 10=maximum disease symptoms, is used here analogously to the assessment of pain. Patients with chronic pain are familiar with this form of assessing the severity of their symptoms by keeping a pain diary.

Example 2

Patient data: 39 years old, female
Duration of the complex pain syndrome: Soft tissue rheumatism 30 years, arthrosis 20 years, neuropathy following nerve injury 5 years
Diagnoses:
1. Soft-tissue rheumatism
2. Severe arthrosis with pain in the right knee joint on resting and exercising. Condition after joint replacements in both hips (arthrosis).
3. Painful mononeuropathy of the left sural nerve with spasticity after irreversible nerve damage.
Local Findings:
Significant swelling and hyperthermia of the right knee joint with intolerable nocturnal resting pain, despite cooling with ice packs and intake of anti-inflammatories.
Right spastic equinus with pasty swelling, here superficial burning sensation and shooting neuralgia. Tender musculature that fatigues easily, tenderness in tendon attachments and soft tissues of most joints.
Therapeutic Response of the Pain:
Despite long-term medication with antidepressants, anticonvulsives and antirheumatics, and the use of walking aids, the most important daily functions were severely restricted, mainly by pain.
Evidence of a Significant Improvement in the Disease Symptoms with Oral Therapy with a Hyperimmunoglobulin Against Endotoxins (LPS) from Egg Yolk from Immunized Chickens (Anti-LPS Hyper-IgY):
Participation in the same study as the patient in Example 1.
After 6 days of IgY treatment with the initial dose of 2×1.25 g, soft-tissue rheumatism was already alleviated and there was an improvement in some of the general quality of life parameters (see FIG. 4). In the last 5 days of the study, a double daily dose (5.0 g in total) again brought about a significant improvement in all pain symptoms, which unexpectedly was also clearly apparent in the neuralgia of the left foot and the resting pain in the right knee joint. There was also a decrease in swelling and hyperthermia here, even when anti-inflammatories were not taken (see FIG. 3).
In the laboratory part of the study, there was a significant reduction of endotoxin-activated monocytes in the peripheral blood (reduction through apoptosis), a decrease in the total number of monocytes to normal values, and quantitative analysis of 22 immuno-messengers (chemokines, cytokines, growth factors) showed a consistent reduction in the plasma concentrations of inflammatory proteins and a significant increase in anti-inflammatory central protein factors.
Withdrawal Attempts:
Treatment with the study preparation was continued, as the positive results could not be achieved by any known alternative means. Efficacy was controlled and confirmed by 2 withdrawal attempts carried out in the course of one year.
Summary:
Oral IgY medication was surprisingly effective on neuropathic pains associated with a mononeuropathy following peripheral nerve damage.
Moreover, in this case the pain, swelling and clinical inflammation signs of activated arthrosis in the knee joint improved subjectively and objectively.
Activated arthrosis is an independent diagnosis with objective radiological and clinical diagnostic criteria, as well as a very clear aetiology and pathogenesis.

Figure 3:
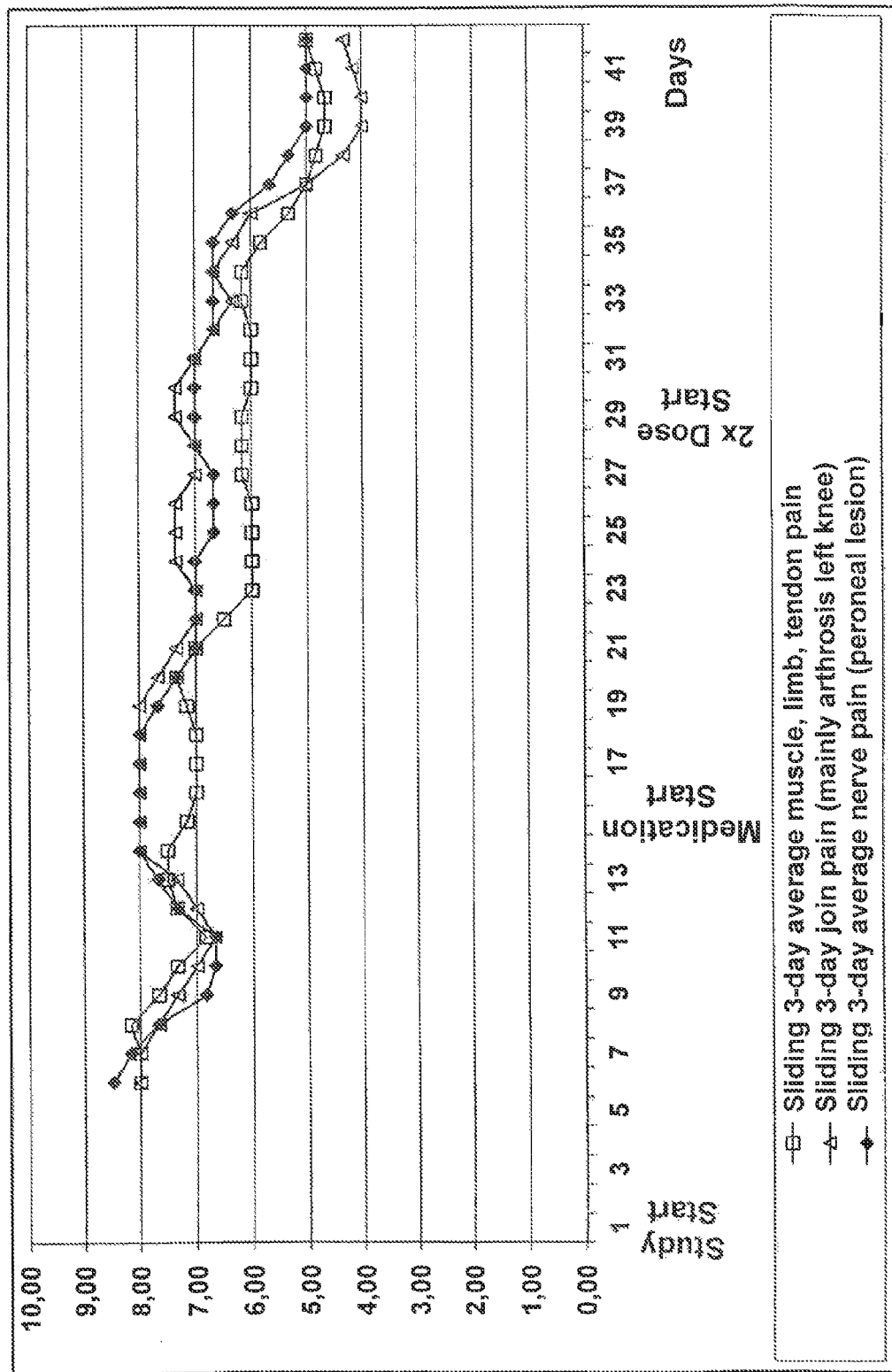
FIG. 3 is a graphical representation of the pain level of 3 pain phenotypes by means of a sliding three-day average.
Figure 4:
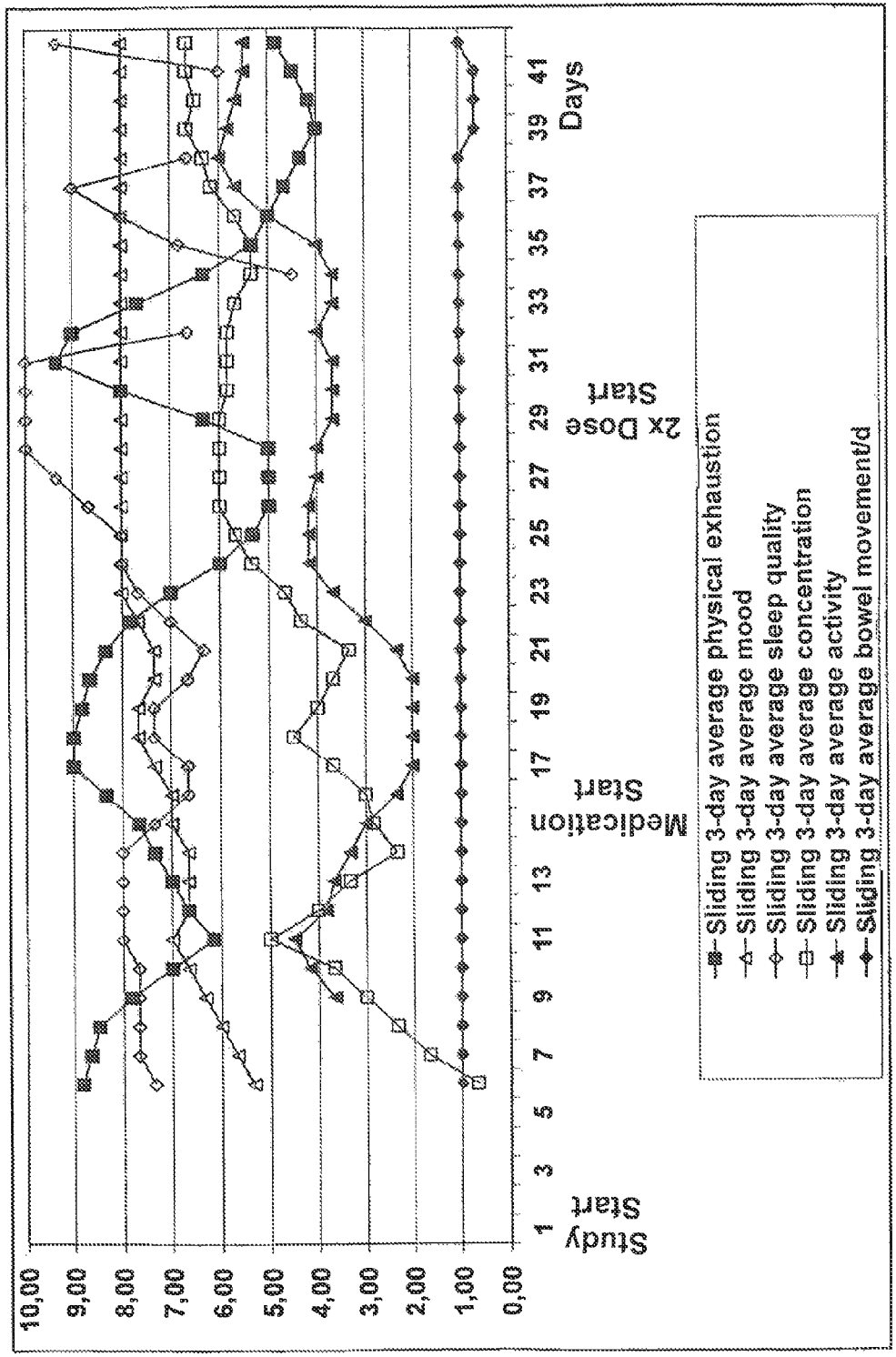
FIG. 4 is a graphical representation of the course of the quality of life parameters (physical exhaustion, concentration ability, mood, activity, sleep quality, bowel movement) for a patient while receiving trial medication, using a sliding three-day average.

The present example provides individual evidence that the endotoxin load of immune cells circulating in the peripheral blood is significantly reduced by orally administered antibodies, and that there is also a causal relationship between the endotoxin load of the blood cells and the inflammatory activation of arthrosis in the knee joint.
For endotoxins at least, such a causal relationship has never been investigated and therefore has also never been proven and is therefore unexpected.
FIG. 3 is a graphical representation of the pain level of 3 pain phenotypes by means of a sliding three-day average. The pain level is determined by the patient in a diary using the NRS method. Each measurement point is the mean value for the 3 preceding days ("sliding three-day average").
FIG. 3 shows that treatment with an anti-LPS hyper-IgY triggers a synchronous reaction
of soft-tissue rheumatic pain (muscle, limb and tendon pain)
of pain in activated gonarthosis on the left (joint pain; mainly arthrosis of left knee)
of neuropathic pain after peripheral nerve damage (right nervus peroneus; neuralgia (peroneal lesion))
FIG. 4 is a graphical representation of the course of the quality of life parameters (physical exhaustion, concentration ability, mood, activity, sleep quality, bowel movement) for the patient while receiving the trial medication, using a sliding three-day average.
FIG. 4 shows that treatment with an anti-LPS hyper-IgY results in a synchronous improvement in
daytime fatigue (physical exhaustion)
concentration ability
range of activity (activity)
mental health (mood).
The severity of disease symptoms is represented by NRS on the ordinate. The measurement points on the ordinate are the mean values of NRS values from the patient diary for the preceding 3 days.

Example 3

Patient data: 56 years old, female
Duration of the complex pain syndrome: 13 years
Diagnoses:
1. Complex regional pain syndrome in both upper extremities
2. Bilateral meralgia paraesthetica=compression syndrome in skin nerves on the outer thigh where the nerves pass under the inguinal ligament.
3. Morton's metatarsalgia in both feet (compression syndrome in the nerves of the sole of the foot between the first and second toes)
4. Irritable bowel syndrome with severe bursts of abdominal pain (colic) predominantly localized in the lower abdomen
5. Painful bladder syndrome/interstitial cystitis (PBS/IC), a bladder disease of unknown aetiology. There is persistent pain in the bladder with a strong urge to urinate even when the organ contains very little urine. It can also be very painful to urinate. There is no evidence of any urinary tract infection or other localized pathology. Endoscopic examination of the bladder mucosa reveals signs of inflammation. The biopsy usually shows an increase in eosinophil granulocyte and mastocyte inflammatory cells, which suggests an allergic inflammation.
6. Neurodermatitis
History and Local Findings:
Following a minor accident, the patient developed a complex regional pain syndrome (CPRS) in the left hand, which spread to the whole of the upper left extremity (shoulder-arm-hand syndrome). This is a combination of the 3 individual diagnoses: periarthropathy of the shoulder joint, epicondylitis humeri radialis, and CRPS of the hand. The patient also had nerve compression syndrome in the bony groove of the ulnar nerve at the elbow with loss of sensory and motor nerve function in the affected hand.

As the disease progressed, the patient also developed compression syndrome in the right metacarpal nerve (carpal tunnel syndrome). Following surgical treatment for this, a complex regional pain syndrome also then developed in the right hand so that in addition to the pain, the patient suffered a complete loss of function of both hands.

Therapeutic Response of the Pain:

While undergoing an unsuccessful daily interdisciplinary pain treatment over the course of 6 months, the patient developed a further compression syndrome of the peripheral nerves in both thighs and feet (meralgia paraesthetica and Morton's metatarsalgia).

The full clinical picture, including neurodermatitis, was eventually treated successfully with intravenous administration of the human C1 esterase inhibitor (C1-INH) Berinert® in combination with low-molecular weight heparin. As the patient did not have a C1-INH deficiency, this was an off-label medication (a treatment outside of approved indications). The treatment had to be continued at intervals of an average of 8 weeks.

Evidence of an Equivalent Elimination of the Disease Symptoms with Oral Therapy with a Hyperimmunoglobulin Against Endotoxins (LPS) from Egg Yolk of Immunized Chickens (Anti-LPS Hyper-IgY):

The patient was only accepted into the IgY therapeutic study already described in Examples 1 and 2 once the effect of the last Berinert® injections had subsided and all of the above disease symptoms, as well as the neurodermatitis and severe headaches, had returned.

Therapeutic Effect:

Within the first week of the study, the initial dose of 2×1.25 g of IgY had completely eliminated headaches and abdominal colic pain. At the beginning of the second study phase (beginning of the third week of treatment with IgY), the neuropathic pain and sensory disturbances caused by nerve compression symptoms in both the lower and upper extremities and shoulder pain and restricted movement had also disappeared (see FIG. 5). The general disease symptoms of the complex health problem and the neurodermatitis disappeared along with the pain, although the daytime fatigue persisted at a low level to the end of the study period. On continuing treatment at the low initial dose, the symptoms of fatigue then also disappeared completely in the following months.

In the laboratory part of the study, there was a significant reduction of endotoxin-activated monocytes in the peripheral blood (reduction through apoptosis), a decrease in the total number of monocytes to normal values, and quantitative analysis of 22 immuno-messengers (chemokines, cytokines, growth factors) revealed significant and successful changes brought about by the treatment, as with all study participants. In this patient, however, the greatest changes were in a different spectrum of chemokines.

Withdrawal Attempts:

Following the study, the study medication was continued at the lower dose over 4 months. Symptoms only returned when the study medication was stopped for a further 3 months.

Summary:

A surprising effect on neuropathic pain occurred, the neuropathic functional disturbances being caused not by injuries to the peripheral nerves but by an almost generalized compression syndrome of the peripheral nerves. This effect occurred within one week at the lowest dose and was equivalent to treatment with Berinert® in terms of quality.

The pain and dysfunction in the shoulder and elbow joint caused by an unusually acute periarthritis and epicondylitis were completely eliminated after 15-16 days. This very common form of inflammatory periarticular disease was indeed associated with the mysterious systemic disease of the patient, but the surprisingly extremely successful response to IgY therapy suggests that the general nature of this disease is a form of the endotoxin-mediated diseases of the locomotor system. It is therefore likely that therapy with antibody preparations, particularly the specific IgY preparation employed, may be promising when used on an as yet unknown proportion of patients with these diseases.

By this analogy, the same can be assumed for irritable bowel symptoms and symptoms of interstitial cystitis.

Even the patient's pronounced neurodermatitis did not return while she was receiving IgY therapy. Irritable bowel syndrome, interstitial cystitis and neurodermatitis have a common immunological feature: pathologically activated mast cells are involved in proven inflammatory organ changes. This cell type of the immune system also has binding sites for endotoxins, so that in particular circumstances these cells can also be activated simultaneously in various organ systems by these toxins. In specific oral antibody therapy with IgY, endotoxins already are partially eliminated in the intestine.

Figure 5:
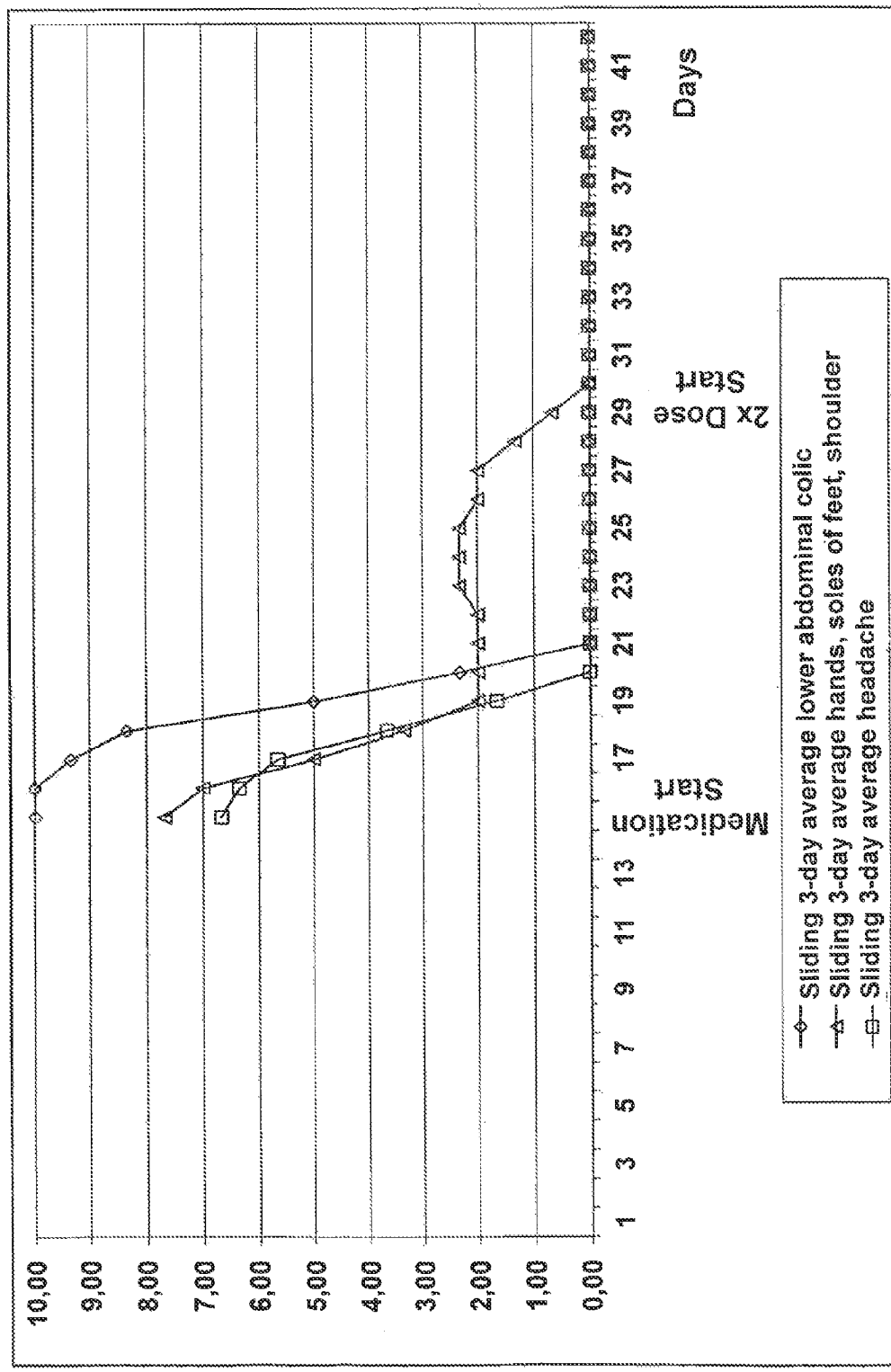
FIG. 5 shows the change in intensity of 3 different classified pain symptoms (the three most acute pain phenotypes) of a patient through self-assessment using NRS values after initial treatment with the specific IgY preparation.

FIG. 5 shows the change in intensity of 3 different classified pain symptoms (the three most acute pain phenotypes) of this patient through self-assessment using NRS values after initial treatment with the specific IgY preparation. The measurement points on the ordinate are the mean values of NRS ratings from the patient diary for the preceding 3 days. The abscissa gives the time in days. The patient began taking IgY on day 15 and the dose was doubled from day 29.

Example 4

Patient data: 55 years old, female
Duration of the complex pain syndrome: 12 years
Diagnoses:
1. Post-zoster neuralgia of the 1st and 3rd right trigeminal branch (trigeminal mononeuropathy after herpes zoster)
2. Migraine without aura
3. Bilateral achillodynia (inflammatory enthesopathy of the Achilles tendon) with signs of autoimmune disease (undifferentiated collagenosis)
4. Irritable bowel syndrome with episodic diarrhoea
5. Secondary antibody deficiency syndrome (IgG and IgA)
6. Laboratory chemistry evidence of an autoimmune disease (autoantibodies) relating to an undifferentiated collagenosis History and Local Findings:

A long time ago (>10 years) the patient had herpes zoster (shingles) on the forehead and upper jaw branch of the right trigeminal nerve, and once the viral infection had cleared, chronic pain, numbness and episode of acute pain persisted, especially behind the right eye, the nose and around the right edge of the tongue (post-zoster neuralgia).

The facial pain attacks continued daily before or after an episode of diarrhoea, which was characterized by a rapid watery bowel movement (irritable bowel syndrome).

The facial pain attacks were also always accompanied by increased perspiration and/or shivering.

Prior to the facial neuralgia, there had already been migraine without aura, which until the start of IgY therapy had occurred with an average of 7 days each month.

At a later stage in the disease, the patient began to suffer from a bilateral achillodynia, which gradually led to significant mobility problems. Achillodynia is a painful disease of the Achilles tendon, which occurs either as an independent inflammatory disease, e.g. after straining the tendon, or as a secondary symptom of a rheumatic disease.

Therapeutic Response of the Pain:

Long-term medication to control the pain consisted of a combination of 6 different drugs: An antiepileptic (pregabalin), 2 antidepressants (amitriptyline and duloxetine), the analgesic flupirtine and the opioids tilidine and fentanyl (200 µg stick as required). The patient had already consulted 9 pain practices, neurology clinics and orthopaedists (for achillodynia). She suffered from all 3 pain syndromes without relief, as well as irritable bowel syndrome and in addition the side effects of the many medications.

Evidence of a Significant Alleviation of the Disease Symptoms with Oral Therapy with a Hyperimmunoglobulin Against Endotoxins (LPS) from Egg Yolk from Immunized Chickens (Anti-LPS Hyper-IgY):

Treatment with the specific IgY was started at the lowest trial dose (2×1.25 g). Once treatment had begun not a single further migraine occurred. The achillodynia and the irritable bowel symptoms also disappeared within one month.

The post-zoster neuralgia was unchanged at this dose, as was medicament use. By doubling the dose (2×2.5 g) after 3 months of treatment at the low trial dose, the facial pain attacks became much less frequent and the duration of the attacks was shortened from one hour to just a few minutes. The intensity of the pain remained unchanged. Some medicaments were dispensed with completely, while others were reduced in dose. The patient's general well-being improved radically.

By substituting the (relatively minor) antibody deficiency with intravenous human immunoglobulins, all the remaining pain and disease symptoms disappeared completely, although numbness in the facial skin and tongue persisted.

Summary:

Post-Zoster Neuralgia

Post-zoster neuralgia is an independent clinical diagnosis of known aetiology. This is a mononeuropathy consisting of permanent nerve damage after a viral infection. Science has not come up with a satisfactory explanation as to why only some patients with shingles go on to develop post-herpetic neuralgia, which often remains untreatable for the rest of a patient's life, after the infection has healed. The binding of endotoxins to the nerve roots damaged by the infection could be one of several mechanisms that are a partial cause of persistent pain. The present case study strongly supports this hypothesis: While being treated with the specific IgY preparation, the patient's migraine, irritable bowel syndrome and inflammatory changes in the Achilles tendon disappeared. Such a significant impact can only be understood in terms of the neutralizing effect of IgY on the transport of endotoxins in the organism. The significant reduction of the duration of facial pain episodes and their reduced frequency suggest that the same induction mechanism at least is involved in this pain syndrome.

Achillodynia

The complete elimination of pain and inflammation in the Achilles tendon in the context of the autoimmune disease is surprising, particularly since no treatment had previously afforded the patient any relief. It is known that inflammatory enthesiopathies (an umbrella term for all inflammatory diseases of the tendon and tendon attachment) are frequently resistant to treatment.

Migraine

The patient's migraine could not be treated adequately with medicamentous seizure prophylaxis (β-blockers) and the specific migraine agents taken by the patient during an attack were not effective enough to enable her to continue to work on days when she had migraines. This resulted in an average of 7 days of absence from work each month solely due to the migraines. This example clearly shows that the transfer of endotoxins has a unique and completely surprising part to play in this condition.

Example 5

Patient data: 65 years old, male, study number 17

Duration of the pain syndrome: Headaches for 35 years, neuropathy of the right sciatic nerve for one year, right epicondylitis for 3 years.

Diagnoses:
1. Persistent symmetrical tension-type headache since a severe episode of "tick-borne encephalitis" (TBE) 1974 (Inflammation of the brain and meninges caused by a virus carried by a tick bite)
2. Epicondylitis humeri radialis and ulnaris right with substantial functional impairment of the entire right arm and severe resting pain.
3. Lumbar back pain radiating across the entire right sciatic nerve, the residual effect of surgical treatment for a herniated disc a year ago (mononeuropathy of the sciatic nerve after pressure injury).

Local Findings:

Very tender periosteum around the muscle attachments of the right forearm muscles on the upper arm in the elbow area. Radiating pain during typical movements with tension on muscle attachments (turning screws, writing, lifting objects with an outstretched arm, such as e.g. hanging coats on door hooks).

Throbbing pain in the lumbar spine, pain in the sciatic nerve when passively raising the right leg in a stretched position while lying down (positive Lasèque's sign), Achilles tendons and right patellar tendon reflex absent, no motor weakness in right leg.

Therapeutic Response of the Pain:

Having taken medication for the meningo-encephalitis for many years with severe side effects (liver damage), the patient no longer takes any medication for his pain. Physiotherapy as part of an in-patient rehabilitation programme (after the meningo-encephalitis and the disc surgery) had no lasting success Evidence of a Significant Improvement in, and in Some Cases Complete Elimination of the Disease Symptoms with Oral Therapy with a Hyperimmunoglobulin Against Endotoxins (LPS) from Egg Yolk from Immunized Chickens (Anti-LPS Hyper-IgY):

During the study there was an improvement in all 3 pain phenotypes, the significant variations in pain level recorded before the study remained, the mean values began to decrease during the low-dose phase (2×1.25 g daily), and this effect was even clearer at the higher dose (2×2.5 g daily). In the follow-up observation phase, the back and sciatic pain disappeared completely while the patient remained on the higher dose. The pain and functional disturbances caused by the epicondylitis were reduced so much that the patient no longer experienced any functional impairment, because the pain was low even under physical stress. During the follow-up phase the headache only occurred early in the morning and it was no longer of significance to the patient (see FIG. 6). In the graphical representation of the numerical figures documented to rate the pain level in the pain diary, the patient had not entered daily average values but rather the maximum values for each day, so that the patient's assessment—relayed verbally—that he was largely pain free is not reflected.

In the laboratory part of the study, the patient showed a comparatively small reduction in endotoxin-activated monocytes in the peripheral blood (reduction through apoptosis), a slight decrease in the total number of monocytes to normal values, and quantitative analysis of 22 immuno-messengers (chemokines, cytokines, growth factors) showed, in comparison to other study participants, a disproportionate reduction in the plasma concentrations of inflammatory proteins (e.g. TNFα, IL-6, IL-8), with the highest values for the increase in anti-inflammatory protein factors (e.g. interleukin 4 and 5).

Withdrawal Attempts:

The patient finished taking IgY after 141 days for a period of 6 months until the headaches and pain of the epicondylitis began to affect quality of life again. Thereafter he took the medication only as needed for periods of 4-5 days, and was then able to control the pain level as desired.

Summary:

Chronic Headache after Meningitis, Mononeuropathy of the Sciatic Nerve after Nerve Root Compression, Epicondylitis The monocyte-bound "endotoxin load" in the patient's blood seems to be implicated in the aetiology of 3 chronic pain phenotypes that are normally diagnosed independently in medicine. The residual damage to the brain and meninges (TBE) following the viral infection, and to the sciatic nerve following root compression are the biological weak points where endotoxin-laden immune cells can become attached and maintain a local immune reaction (cause of pain). The causal explanation for this epicondylitis is an immune activation in the neural supply of the right arm (and not the painful elbow).

Figure 6:
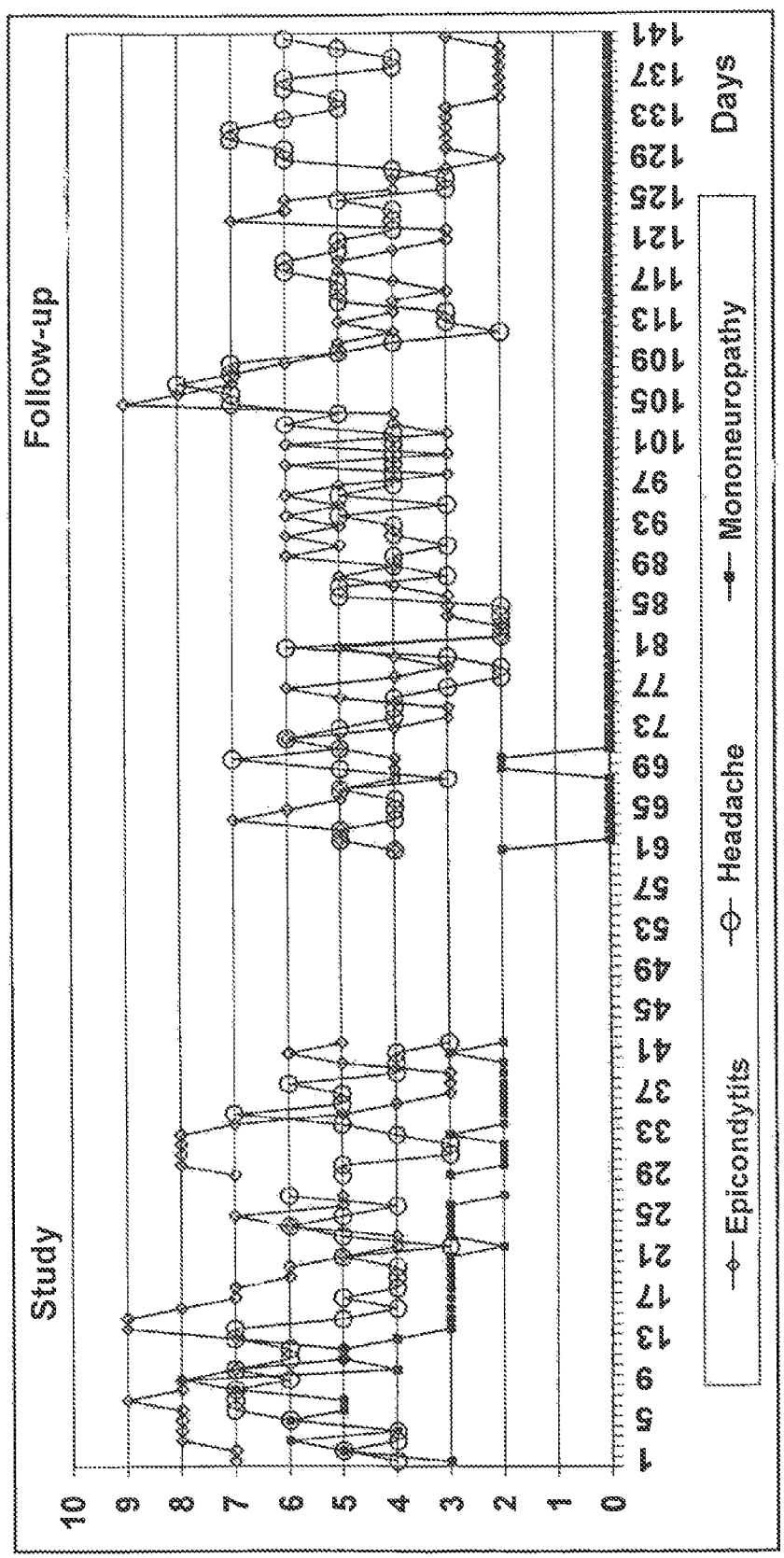
FIG. 6 illustrates the changes in intensity of 3 different classified pain symptoms (epicondylitis, headache and back-sciatic pain/mononeuropathy) of a patient based on self-assessment of NRS scores over a study period and during subsequent follow-up, when the patient continued to take IgY at a low maintenance dose until day 141.

FIG. 6 illustrates the changes in intensity of 3 different classified pain symptoms (epicondylitis, headache and back-sciatic pain/mononeuropathy) of this patient based on self-assessment of NRS scores over the study period and during subsequent follow-up, when the patient continued to take IgY at a low maintenance dose until day 141.

The measurement points on the ordinate correspond to NRS values that were taken from the diary (there was no 3-day average due to relatively low fluctuations in the pain level). The abscissa gives the time in days. IgY treatment began on day 15 and continued in double the dose from day 29 to day 42. Thereafter the treatment was continued at a low maintenance dose until day 141.

Example 6

Patient data: 65 years, male
Duration of the pain syndrome: 11 years with interruption of symptoms for 3.5 years after an operation (the Jannetta procedure).
Diagnoses:
  1. Trigeminal neuralgia, II. and III. right branch (diabetic mononeuropathy)
  2. Type I diabetes stabilized with insulin pump, diabetic distal leg polyneuropathy, diabetic nephropathy (proteinuria, still normal function)

History and Local Findings:

The neuralgia began more than 10 years after onset of diabetes, initially responding to carbamazepine, then additionally other anticonvulsants, and finally microvascular decompression of the trigeminal root (MVD or synonymously: the Jannetta procedure). 3.5 years pain-free. When the attacks began again, the dose of carbamazepine was increased rapidly, leading to pronounced side effects affecting the central nervous system, with the threat of disability (threatened loss of driving licence, professional driver).

Finding:

Tingling malaise in a small area of the upper lip and the oral mucosa of the cheek in the lower jaw. Strongly avoids creating air currents or contact that might trigger pain attacks in these areas. Repeated daily bursts of pain in quick succession brought on by eating, but still just tolerable with toxic blood levels of the antiepileptic drug (apparently low level of pain at the start of the study in FIG. 7). Work-related stress and personal issues increased the likelihood of an attack.

The distal leg polyneuropathy is purely sensory and consists of the sensation of walking on cotton wool, and oedemas in the feet and lower legs.

Evidence of Complete Remission (Elimination) of the Trigeminal Neuralgia and Improvement of Symptoms of the Diabetic Polyneuropathy with Treatment with the Hyperimmunoglobulin Against Endotoxins (LPS) from the Egg Yolk of Immunized Chickens (Anti-LPS Hyper-IgY):

Within the first 14 days of study, at an IgY-dose of 2×1.25 g per day, the patient was already pain-free, and the patient reduced the carbamazepine dose from 1,200 mg to 900 mg with the effect that, while he no longer suffered from the side effects, the attacks began to recur. On a doubled dose of IgY of 2×1.25 g daily, the patient was again pain-free, and carbamazepine was reduced to a daily dose of 450 mg for the remainder of the study (see FIG. 7). The sensory symptoms in skin and mucosal areas, which were the main sites of the pain attacks, disappeared completely during IgY therapy. For idiopathic trigeminal neuralgia there are no sensory disturbances, with the exception of therapeutic interventions that cause damage to the nerves. This case was therefore a diabetic mononeuropathy in the area of the trigeminal nerve, and not an idiopathic form of neuralgia.

While on IgY therapy, the patient also recovered the sensation in both feet, and the tendency towards oedema in the feet and lower legs was significantly lower. In these regions of diabetic polyneuropathy, the patient had no pain. The effect on symptoms of polyneuropathy is surprising.

Thereafter, the patient, while taking a daily dose of IgY of 5 g, was able after one month to stop taking the antiepileptic drug carbamazepine completely and remained symptom-free on an IgY maintenance dose of 2.5 g of IgY per day. On repeated attempts to lower this daily dose, the sensory disturbances returned in the same places that the patient typically knew as heralding pain attacks.

In the laboratory part of the study the patient showed a significant reduction of endotoxin-activated monocytes in the peripheral blood (reduction through apoptosis), and a significant decrease in the total number of monocytes. Quantitative analysis of 22 immuno-messengers (plasma concentrations of chemokines, cytokines, growth factors) showed a significant reduction in growth factors IGF-1 and GMCSF and proinflammatory cytokines IL-8 and IL-7, and an increase in anti-inflammatory cytokines IL-4, IL-5 and IL-13 in the patient.

Withdrawal Attempts:

The patient could only reduce the dose of study medication (5 g daily dose of IgY), a period without treatment was not possible. The specificity of the effect of the dominant set of antibodies against endotoxins was compared with a therapy involving a hyperimmune IgY preparation against antigens of periodontosis pathogens.

Summary:
Diabetic Mononeuropathy of the Trigeminal Nerve

The sustained elimination of the symptoms of idiopathic trigeminal neuralgia through long-term treatment with oral immunoglobulins from bovine colostrum is already known, but not for trigeminal neuralgia on the basis of diabetic mononeuropathy, as in this example.

Diabetic Polyneuropathy

In this example, the concomitant therapeutic influence on the sensory and autonomic components of polyneuropathy (loss of sensation and lower leg oedemas) gave the first surprising indication of the effectiveness of the preparation in diabetic polyneuropathy.

Figure 7:
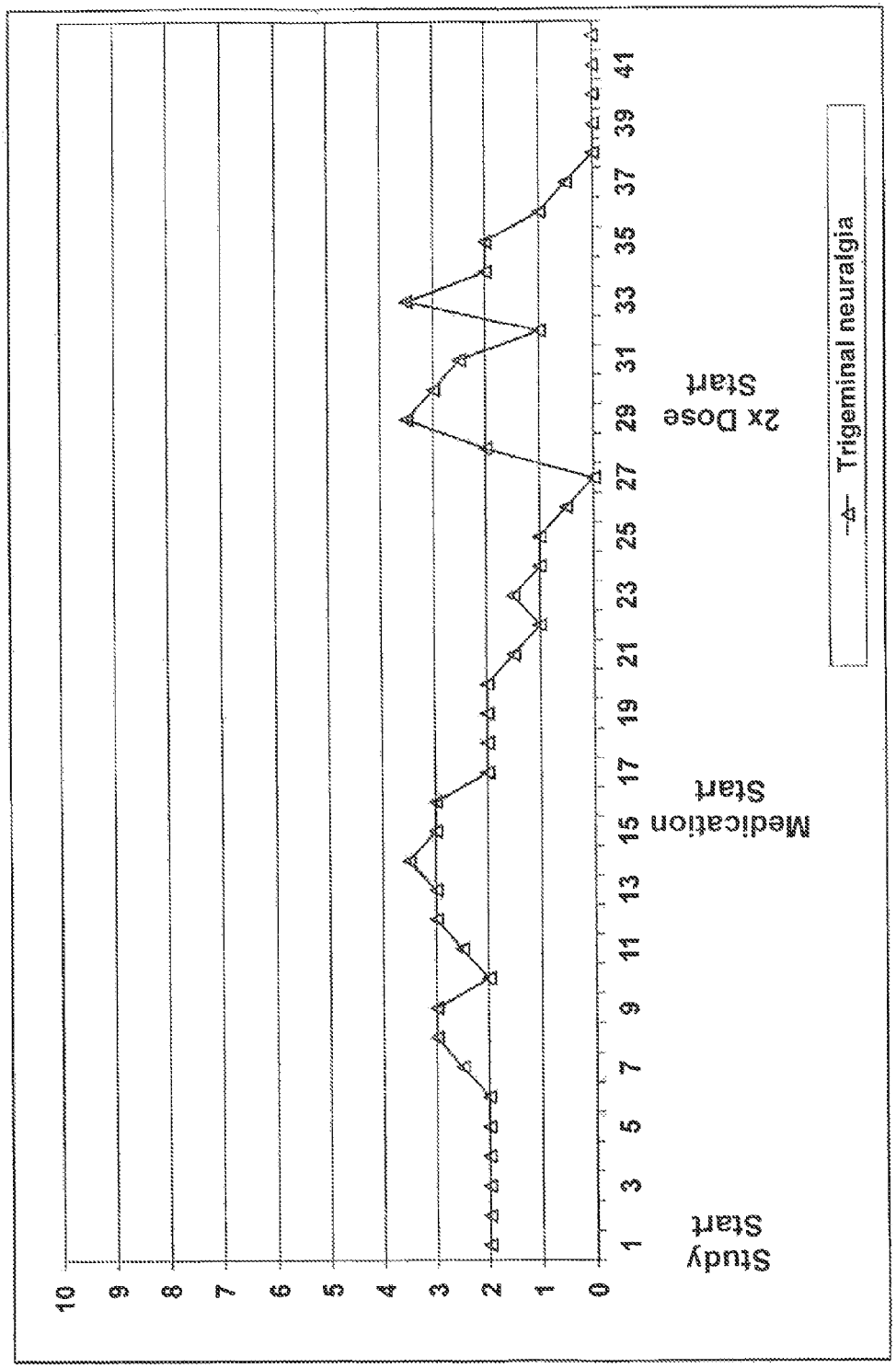
FIG. 7 illustrates changes in the intensity of pain attacks resulting from trigeminal neuralgia by means of patient self-assessment using NRS scores for a study period.

FIG. 7 illustrates changes in the intensity of pain attacks resulting from trigeminal neuralgia by means of patient self-assessment using NRS scores for the study period. The ordinate shows the self-assessment of the pain level by the NRS for each day. The study days are shown on the abscissa. Treatment began on day 15 and continued at double the dose from day 29. Before IgY therapy, pain had been poorly controlled with carbamazepine in a daily dose of 1,200 mg, which had already resulted in toxic levels of the drug in the blood. On starting IgY therapy (from day 15), the carbamazepine dose was reduced at intervals until the end of the study, down to a daily dose of 450 mg (day 42). At the end of the study the patient was symptom-free. Carbamazepine was completely discontinued thereafter.

Example 7

Patient data: 43 years old, female
Duration of the illness: 9 years
Diagnoses:
1. Complex regional pain syndrome of lower right extremity
2. Idiopathic back pain
3. Exceptionally severe irritable bowel syndrome, complicated by daily uncontrolled bowel evacuation during stomach cramps
4. Painful bladder syndrome/interstitial cystitis (PB/IC), also with bladder cramps and uncontrolled urination History and Local Findings:

After hallux valgus surgery on the right foot, 5 further attempts at a cure by surgery were carried out as a result of lingering postoperative extremely severe neuropathic pain presenting as a complex regional pain syndrome that would not respond to medicaments The pain improved with multimodal pain therapy with limited strength in the foot.

Following unsuccessful attempts to treat the inflammation and extreme pain with medicaments, (long-term antibiosis owing to suspected chronic infection, anti-inflammatory long-term medication), the existing irritable bowel symptoms became completely uncontrollable. The intestinal colic was associated with watery stools, which were mainly passed in bed at night in an uncontrolled manner. The painful bladder spasms led to loss of control of the sphincter muscle.

Evidence of a Significant Remission (Elimination) of Bowel and Bladder Disease Symptoms with Treatment with the Hyperimmunoglobulin Against Endotoxins (LPS) from Egg Yolk from Immunized Chickens (Anti-LPS Hyper-IgY):

The neuropathic pain symptoms in the right foot had already improved under previous multimodal therapy (combined partial in-patient treatment, involving psychological, physio- and drug therapy), and only improved slightly during treatment with the study preparation. The foot could still no longer bear any load. Back pain, particularly severe in the neck and shoulder area and the lumbar-sacral region, improved lastingly by 2 points on the numerical rating scale. The bowel and bladder spasms disappeared completely towards the end of the IgY study on a daily dose of 5 g of the specific IgY preparation. The number of daily bowel evacuations fell from an average of 9 (2-17) to 2 (see FIG. 8), the stool no longer contained any undigested food constituents, and was formed. Uncontrolled bowel movements and urination ceased completely.

Thereafter, the results of the treatment were maintained over a year with a daily dose of IgY of 4 g.

In the laboratory part of the study the patient showed typical responses to treatment, in particular a significant reduction of endotoxin-activated monocytes in the peripheral blood (reduction through apoptosis) and a significant decrease in the total number of monocytes. In the quantitative analysis of 22 immuno-messengers (plasma concentrations of chemokines, cytokines, growth factors), a significant reduction in growth factors IGF-1 and GMCSF and proinflammatory cytokines IFN-γ, TNFαR-1, IL-8 and IL-6, and an increase in anti-inflammatory cytokines IL-4, IL-5 and IL-13 are to be singled out.

Withdrawal Attempts:

Several attempts were made to end IgY-therapy, but each time the bowel and bladder symptoms returned after a few days.

Summary:
Irritable Bowel Syndrome, Painful Bladder Syndrome/Interstitial Cystitis (PBS/IC), Also Symptoms of an Autonomic Neuropathy Irritable bowel syndrome of this severity is certainly a rarity, as is the combination with comparable bladder symptoms. 9 years of failed attempts to treat the foot and the extreme pain with medicamentous therapy has resulted in considerable damage to the barrier function of intestinal mucosa and certainly promoted and contributed to the unusual extent of the disease. The over 90% endotoxin-activated blood monocytes (CD14+ and CD45+) before the IgY treatment ultimately reveal the consequences of this barrier damage, which with the insufficient apoptosis of antigen-receiving monocytes in the intestine has led to an abnormally high endotoxin load in the whole organism. In laboratory tests at the end of study, monocytes with endotoxin binding (CD14+) had fallen to 65% and the "activated" monocytes (CD45+) had fallen to 10%. The simultaneity of the bowel and bladder symptoms with significant dysfunctions of the sphincter muscles of both organs suggests that endotoxins were the primary cause of an autonomic neuropathy. Bowel and bladder pain and dysfunctions could therefore largely be interpreted as damage to the autonomic nerve supply of both organ systems under the influence of endotoxins.

Figure 8:
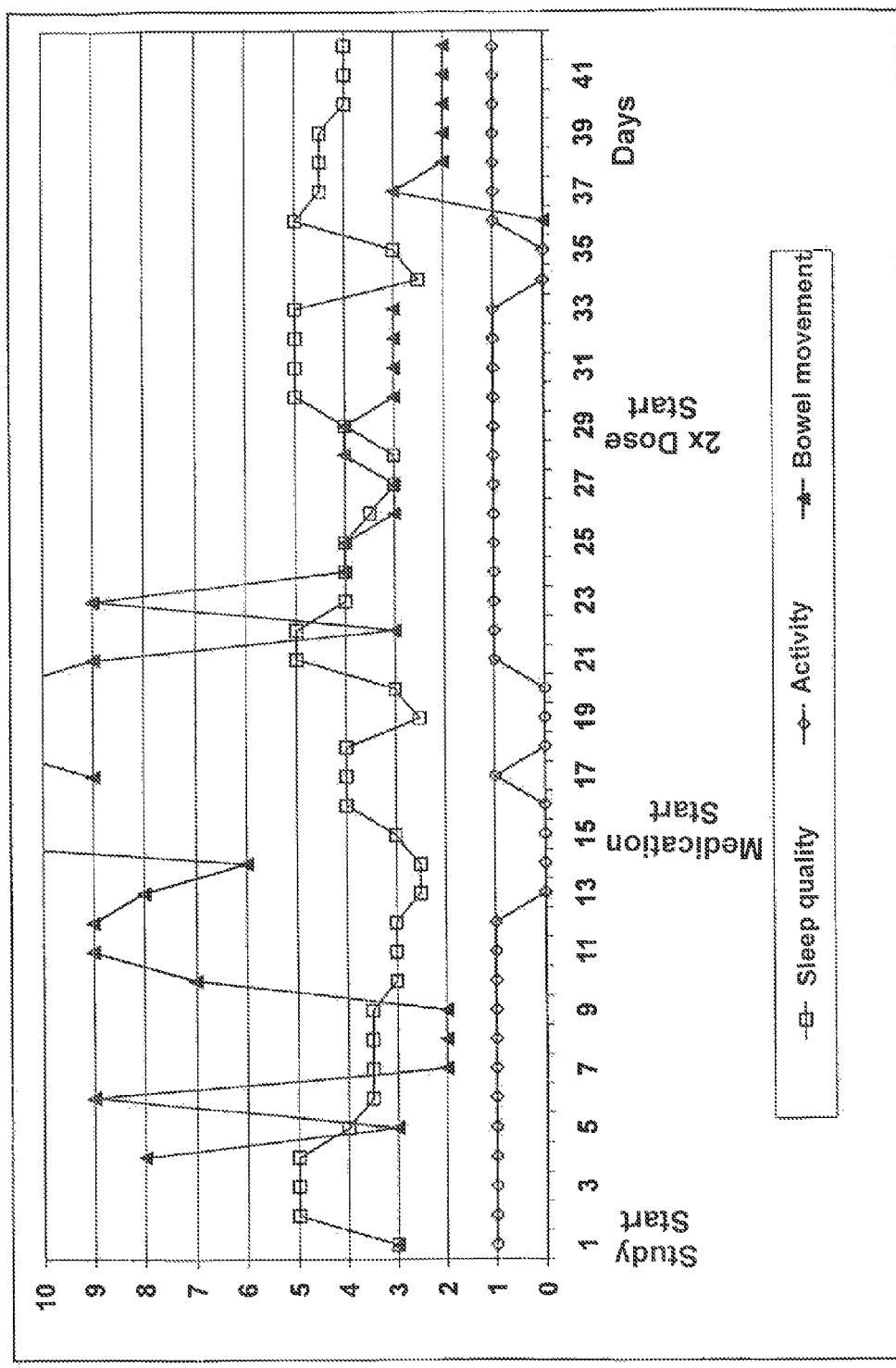
FIG. 8 shows the action/effect of the IgY preparation on 3 quality of life parameters (sleep quality, activity and bowel movement) in a patient, who had an extreme manifestation of irritable bowel syndrome with diarrhea.

FIG. 8 shows the action/effect of the IgY preparation on 3 quality of life parameters (sleep quality, activity and bowel movement) in this patient, who had an extreme manifestation of irritable bowel syndrome with diarrhoea.

The ordinate shows the self-assessment score for "sleep quality" and "activity" using NRS daily values and the daily number of bowel movements.

The abscissa shows the time in days. The study medication was started in day 15, and continued in double the dose from day 29 to day 42.

Example 8

Patient data: 55 years, male
Duration of the illness: 19 years
Diagnoses:
1. Post-Lyme borreliosis syndrome with signs of chronic encephalitis, condition after Lyme carditis
2. Polyneuropathy 3. Irritable bowel syndrome with diarrhoea
4. Chronic exhaustion/fatigue syndrome (CFS)
5. Polymorphic photodermatosis History and Local Findings:

Erythema chronicum migrans, subsequently Borrelian radiculitis (Garin-Bujadoux-Bannwarth syndrome), encephalitis, and polyneuropathy. Oral and intravenous long-term antibiosis resulting in severe intestinal symptoms caused by bacterial overgrowth. Full disability because of the pain and the extreme form of CFS.

Thereafter: Onset of polymorphic photodermatosis

Intermittent treatment of nerve pain (polyneuropathy) with polyvalent human immunoglobulins (IVIg). This therapy gave substantial control of the pain and CFS and resulted in a marked improvement in the photodermatosis. Further improvement in the photodermatosis after eradication of chronic *Helicobacter pylori* infection of the stomach (duration of the improvement: 6 months).

Thereafter the IVIg no longer had a curative effect. The patient lived in a completely darkened room, with only UV-B-free artificial light. Largely bedridden, home care.
Evidence of a Significant Improvement in the Polyneuropathy, Photodermatosis, CFS and Irritable Bowel Syndrome with Treatment with the Hyperimmunoglobulin Against Endotoxins (LPS) from Egg Yolk of Immunized Chickens (Anti-LPS Hyper-IgY):

Admitted to in-patient care at the Dermatological University Clinic Würzburg.

Admitted to a completely daylight-proof single room. Continued pain therapy (polyneuropathy) with gabapentin, starting treatment with the specific IgY preparation in a daily dose of 2×1.25 g. This resulted in a significant improvement in neuropathic pain and complete normalization of bowel movement. After one week, the IgY preparation dose was increased to 3×1.5 g daily. On this treatment, there was a daily increase in exposure to daylight from 300 to 9,000 lux per day until discharge for home care after 4 weeks.

Summary:
Polyneuropathy after Neuroborreliosis, Chronic Exhaustion/Fatigue Syndrome (CFS), Irritable Bowel Syndrome, Polymorphic Photodermatosis All the disease symptoms were controlled by IVIg over a 6-year period, to the extent that although the patient remained unable to work, he was largely self-sufficient. Even under optimum conditions, i.e. in the first 4 weeks after each intermittent treatment of 30 g of IVIg, the patient could not walk more than 500 m 3 times per day. The exercise limits were determined by increased pain, exhaustion symptoms, and extremely itchy inflammatory skin changes when the low light tolerance threshold was exceeded. Skin changes, once they appeared, took weeks to heal. The antiepileptic gabapentin provided minimal relief within narrow limits at least for the itching. Antihistamines and cortisone brought no relief.

Polyneuropathy

The polyneuropathy was characterized by shooting pains when moving, which were projected into regions of the body with reduced sensitivity, mainly in the left hemisphere of the body. In addition, there was symmetrical pain in the 2nd and 3 trigeminal branches caused by chewing or touching of the skin (trigeminal neuropathy). During treatment with IgY, symptoms of trigeminal neuropathy disappeared completely, and other pain was reduced so much that, despite the very weak condition of the patient, activities such as getting out of bed, dressing, showering, writing and walking short distances were possible without any pain.

CFS

The severe daytime fatigue, which throughout the disease was only periodically interrupted when the patient was being treated with IVIg, was alleviated under therapy with IgY to the extent that the patient was able to participate in most day-to-day activities without needing a break.

Irritable Bowel Syndrome

Irritable bowel syndrome consisted of abdominal spasms and frequent evacuation of unformed stools. Notably, the patient reported that he was never able to fully empty the rectum, and that for half-hour or longer after bowel movements small semi-liquid quantities were still passed unnoticed, so he was forced to wear pads. This loss of control over bowel evacuation was a clinical sign of autonomic neuropathy. These symptoms already disappeared in the first week of treatment with IgY.

Polymorphic Photodermatosis

The polymorphic photodermatosis was extremely acute. Testing a small area of skin with a defined dose of UV-B already produced a vigorous localized reaction with the typical dermatological results of the disease.

The response of this particularly severe clinical condition to IVIg is described in case reports, as are successful treatments by plasmapheresis (plasma exchange treatment).

The significant partial success of treatment with anti-endotoxin hyperimmune IgY on the one hand is very surprising, and on the other provides evidence of the involvement of endotoxins in the aetiology of this individual example.

Example 9

Patient data: 59 years, male
Duration of the illness: 6 months
Diagnoses:
1. Carcinoma of the floor of the mouth (right side), operated, irradiated
2. Diabetes mellitus type I
3. Neutropenia, anemia (as a result of radiotherapy)
4. Neuropathic facial pains
5. Mucositis of the irradiated oral mucosa History and Local Findings:

Since radiotherapy of the operated area in the region of the right lower jaw/floor of the mouth, the patient had experienced acute bouts of facial pain radiating from the lower jaw into the right ear, brought on by swallowing. Severe burning sensation in the oral mucosa in the irradiated area.

Resting pain largely controlled with tramadol+metamizole. Almost impossible to eat because of pain.

Initially treatment with 6.4 g of subcutaneous immunoglobulin. After just a few hours the neuropathic facial pain was alleviated, but not the local contact pain of the oral mucositis.
Evidence of a Significant Improvement in the Mucositis, Unhindered Oral Intake of Food while being Treated with the Hyperimmunoglobulin Against Endotoxins (LPS) from Egg Yolk of Immunized Chickens (Anti-LPS Hyper-IgY):

Immediate response of contact pain in the inflamed oral mucosa on drinking and eating. Normal food intake largely restored.

Summary:

The bacterial colonization of the oral mucosa may contain endotoxin-producing germ populations. The sensory nerve endings of the trigeminal nerve carry binding sites for endotoxins (Toll-like receptor 4), so that endotoxins can cause extreme pain hypersensitivity in inflamed mucosal lesions. The binding of the endotoxin by locally administered antibodies eliminates not only the pain but also the inflammation caused by endotoxins. Unlike local anaesthetic measures, the antibodies also accelerate healing.

The abovementioned examples were all carried out with the antibody preparation from Preparation Example 1. The therapeutic successes for the uses according to the invention are not limited exclusively precisely to this Preparation Example 1. Preparation Example 2 was employed in the following examples. It is moreover probable that even better results can be achieved with alternative preparations than with the Preparation Examples 1 and 2 employed. It is of course possible here for the person skilled in the art to optimize the preparation composition in the context of the agent to be used or the preparation for individual indications or even where appropriate for individual patients. It is accordingly of course clear to the person skilled in the art that the use according to the invention relates not only to Preparation Examples 1 and 2 employed in the examples, but the surprising effects are also to be expected with other agents or preparations to be used according to the invention.

Example 10

Patient data: 13 years old, male
Duration of the disease 6 months
Diagnoses:
 1. Acute right periarthritis humero-scapularis (rotator cuff tendinitis)
History and Local Findings:
For about 1 week the patient has been suffering from increasing movement pain in the right shoulder joint. After 5 days an additional nocturnal rest pain occurred and after 6 days complete inability to use the right arm. Bending in the elbow joint is so painful that independent dressing and closing of the first are impossible (shoulder pain triggered).

The youth cannot remember a triggering trauma or excessive strain. The history shows only an allergic asthma, which did not exist, however, at the start of the pain symptoms.

The right shoulder joint is extremely painful to pressure in the region of the entire rotator cuff. Compared with the opposite side, an increase in temperature is also to be found here. A slight diffuse swelling of the soft tissue around the shoulder joint into the region of the upper shoulder blade is moreover to be observed. Any active movement of the arm and hand is avoided by the patient. The passive mobility of the shoulder joint is limited maximally because of pain being triggered in all movement axes.

These were typical symptoms of an idiopathic acute periarthritis which was hitherto untreated.
Evidence of a Complete Cure of the Periarthritis Under Treatment with the Hyperimmunoglobulin Against Endotoxins (LPS) from Egg Yolk of Immunized Chickens (Anti-LPS Hyper-IgY):

Therapy was conducted by administration of 2×½ sachets of IgY effervescent powder (daily dose; corresponds to 2×2.5 g of antibody mixture). No analgesics were prescribed or taken.

First follow-up consultation on the morning after the start of therapy:

The patient had slept through the night again, could already dress himself independently in the morning and also tie his shoes. Greeting with a cautious handshake was possible, as well as spontaneous bending of the elbow joint, without considerable pain being triggered in the shoulder.

Within 5 days a continuous improvement to absence of symptoms occurred. A total of 7 sachets of the IgY preparation were taken. The last consultation with the patient took place after a further 6 weeks. No recurrence of the symptoms occurred.
Summary:

This was an acute idiopathic periarthritis of a shoulder joint without prior treatment. The IgY therapy led to a rapid cure without trace, which already started with the first dose and was complete after 5 days.

Example 11

Patient data: 51 years old, male
Duration of the illness 7 years
Diagnoses:
 1. Pemphigus vulgaris
History and Local Findings:
The disease has existed for 7 years. It is a rare autoimmune disease of the skin and mucous membranes. The manifestation in the region of the oral mucous membrane causes losses of the mucous membrane over large areas, which leaves behind extremely painful ulcers (in the sense of mucositis) which heal only under chemotherapy of the disease.

During this period oral intake of food and liquid is scarcely possible.

It has so far been possible to interrupt the disease in ever longer phases by chemotherapy. However, all attempts to gradually reduce the chemotherapy resulted in recurrences, which usually started in the region of the oral mucous membrane.

Since treatment of the oral mucous membrane with IgY it has been possible to maintain oral nutrition in the last two bouts of the disease, since the pain already started to largely subside a few hours after the start of intake.

In the last few days the patient has found small areas of painful mucous membrane defects in the mouth again, a sure sign of a renewed recurrence of the disease.
Individual Healing Attempt with IgY:

A local symptomatic therapy with IgY effervescent powder in a dose of 2×1.25 g per day (IgY preparation from Preparation Example 2) was first carried out until food intake was possible again unimpeded and without pain (maximum of one week).

Thereafter treatment with the enteric presentation form of the IgY preparation was started with the intention of eliminating LPS as possible triggers of the systemic disease already in the region of the small intestine.

Dosage: 3×3 enteric tablets daily for the duration of one month (corresponds to almost 3.4 g daily of IgY preparation from Preparation Example 2).

During this time the oral treatment with IgY effervescent powder was continued in a minimal dosage to maintain the intact oral and pharyngeal mucous membrane.

The materials required in the 1st month: daily 3×3 enteric tablets (almost 3.4 g daily dose of the IgY preparation from Preparation Example 2). 270 enteric tablets and 37 daily dose units of effervescent powder are made available.

The decision to continue the treatment in the same or a changed dose takes place at the end of each monthly period. The therapeutic effect is checked by diary entries of the symptoms of the disease, course and dose of the immunosuppressive chemotherapy.

This is the first attempt at therapy of a patient suffering from pemphigus vulgaris with IgY. Treatment of the mucositis (oral mucous membrane) of this patient was successful on every application in the past.
Further Course of the Disease Under Treatment with IgY (Status: Oct. 3, 2012):

After the painful mucosal lesions of the oral/pharyngeal cavity had subsided under administration of IgY effervescent powder, a considerable improvement in general well-being already occurred 4 days after the start of taking the enteric tablets (3×3 tablets daily).

Complete elimination of the chronic exhaustion symptoms

Re-established physical capacity

Elimination of non-specific joint pain in the region of the shoulder girdle

At the next analysis of the specific antibody titre (autoantibodies) in the University Dermatology Clinic, the lowest titre since the start of the disease (1:300) was measured. Before the treatment this titre was >1:10,000.

After taking blood to determine the immunological activity parameters under the optimum clinical state, the IgY therapy was ended after 6 months.

After a therapy pause of almost 4 months, symptoms of the pemphigus vulgaris arose again for the first time at the end of February 2012 (oral mucosal lesions and blisters on areas of skin in the region of the upper part of the body). Non-specific joint pain and mild exhaustion symptoms preceded the recurrence of the autoimmune disease.

Blood was taken again for analysis of the autoantibodies and the immunological activity parameters. The titre of specific autoantibodies had risen only slightly (1:400).

Treatment with IgY was resumed again. 1 sachet of effervescent powder per day and 3×3 enteric tablets were administered (corresponds to a daily dose of almost 8.4 g of the IgY preparation from Preparation Example 2).

The non-specific pain symptoms disappeared within a few days and the (slightly pronounced) erosions of the oral mucous membrane healed rapidly. No new blisters occurred on the skin and the old ones healed within 14 days.

In this Course a Healing Effect of the IgY Preparation on the Entire Symptoms of the Autoimmune Disease is Now without Doubt to be Recognized.

The recurrence of the disease after a 4-month pause in the therapy could be suppressed for the first time without using dexamethasone and mycophenolate mofetil.

Example 12

Patient data: 41 years old, female
Duration of the disease 9 months (after bone marrow transplant (BMT) because of leukaemia)
Diagnoses:
1. Chronic graft-versus-host disease (GvHD).
History and Local Findings:
9 months after the BMT a chronic GvH developed in the oral and genital mucous membranes and a GvH keratoconjunctivitis. Short time later: acute involvement of the lungs in the GvH with global insufficiency of the lungs requiring ventilation. After surviving the lung GvH a long-term therapy was carried out with prednisolone in a daily dose of between 20 and 30 mg, in addition to the chemotherapy of the leukaemia. The cortisone administered leads to a pronounced Cushing's disease syndrome.

The chronic GvH of the mouth and eyes and of the vaginal mucous membranes allows no reduction in the cortisone dose below 20 mg. The lung is currently not affected, but still subject to significant restrictions in function.

From March/April 2011 oral IgY therapy was started with a daily dose of 2 teaspoons of powder (corresponds to approx. 2.5 g of IgY preparation from Preparation Example 2) in a vanilla yoghurt. An improvement in the mouth and eye involvement was to be observed, but not in the genital GvH symptoms. The amount of prednisolone administered could be reduced to a daily dose (DD) of 15 mg.

A "wash out" phase followed for the duration of one month.

Individual Treatment Plan of the Therapeutic Attempt with Enteric IgY Tablets and (Optionally) IgY Effervescent Powder.

The treatment plan provides for initially administration of 3×3 enteric tablets daily (daily dose of almost 3.4 g) for the duration of 4 weeks in the 1st month. 270 enteric tablets of IgY are provided in the 1st month.

All the symptoms of the GvH are recorded. Under consultation with the treating oncologist and depending on the clinical findings, the dose of corticoid administered and therefore the accompanying immunosuppression are to be reduced. In the event of clinical remission of the GvH symptoms, the therapy is continued in the same dosage until the cortisone therapy has been gradually phased out completely. If remission of the symptoms is not complete or it is necessary to maintain the cortisone medication, additional taking of effervescent powder is envisaged in the next step for the duration of a further 4 weeks. 270 enteric tablets of IgY are provided in the 2nd month.

The treatment plan furthermore provides for an identical dose of enteric tablets (3×3 tablets; almost 3.4 g daily of Preparation Example 2) for the duration of a further 4 weeks in the 2nd month to be administered, and the additional dose of 2×½ sachets of effervescent powder (5 g of IgY preparation from Preparation Example 2) (in each case based on the daily dose. The question of whether the oral action brings an additional benefit for the oral and possibly also the conjunctival manifestation is to be investigated. 270 enteric tablets and additionally 30 sachets of "effervescent powder" of IgY are provided for the 2nd (and where appropriate 3rd) month.

If an overall optimum action does not occur, the dose of the enteric IgY tablets is to be increased to 3×4 tablets (daily dose of 4.5 g of IgY preparation from Preparation Example 2) for the duration of a further 4 weeks and additional effervescent powder is to be administered only in the event of prior benefit. 360 enteric tablets and additionally a further 30 sachets of "effervescent powder" of IgY are provided for the 4th month.

If a complete remission of the GvH without cortisone medication results for any period of at least 1 month, the dose is to be reduced down to the maintenance dose by 3×1 tablet (daily dose) in weekly steps. The maintenance dose is then still to be determined.

The corner times of blood samples (if necessary also stool samples) are:
1. At the end of the "wash out" phase and before the start of the first 4-week period, while the enteric IgY tablets are being administered
2. After the first 4-week period
3. After discontinuation of cortisone
If a remission occurs
If clinical symptoms return when the dose is reduced.

In the event of a positive action, the patient can continue to receive the preparation in a dose according to requirements. In the event of complete remission of the symptoms over a period of 2 months, a withdrawal is attempted.

The GvH symptoms have been recorded by the patient in a diary since the beginning of March 2011 by a visual analogue scale (pain) and the visible symptoms documented by the specialist.

This was the first attempt at therapy of a chronic GvH with IgY.

Results of this Individual Healing Attempt:

Because of an unforeseen increase in the tumour markers in April 2011 and the associated need for a rapid exit from the cortisone medication, the first blood sample was already taken 4 weeks after the end of the test phase with IgY effervescent powder. The cortisone medication had already been discontinued at this point in time and the IgY therapy was then started, in contrast to the original treatment strategy, immediately with 3×4 tablets of the enteric formulation combined with one sachet of effervescent powder.

The acute increase in the tumour markers was a typical consequence of the high-dosed cortisone medication which was necessary to suppress the GvHD. Cortisone inhibits not only the graft-versus-host reaction (GvHR), but to the same extent also the antitumour activity of the donated bone marrow (inhibition of the graft-versus-tumour activity).

Under this therapy there was a constant improvement in all the disease symptoms of GvHD (in spite of discontinuation of cortisone). The tumour markers could soon no longer be detected in the blood. The chemotherapy was therefore decreased stepwise to a minimal dosage. In August 2011 the patient resumed her employment after 1½ years, and in January 2012 in the state of an almost complete re-establishment of capacities blood was taken a second time for analysis of the immunological activity parameters.

The IgY therapy is being continued in the combination of the effervescent powder with the enteric tablets in a slow reduction of the dose. If the positive state continues to remain stable, complete exit from oncological drug therapy is planned.

Example 13

Patient data: 55 years old, male
Duration of the illness 18 months
Diagnoses:
  1. Bilateral chronic epicondylitis (more acute on the right side)
History and Local Findings:

The patient is a sports teacher, swimming team trainer and sports therapist in a physiotherapy practice. The epicondylitis has existed for 18 months, initially only on the right, in the further course of the disease on both sides more acute on the right, always limited to the radial epicondylus.

Treatments to date have taken place in an orthopaedic practice. Antiinflammatory oral drugs provided no relief. Local injections with local anaesthetics and cortisone led to alleviations, which for some time have lasted a maximum of one day. Physiotherapy, tapes and other aids were not able to influence the progress of the symptoms.
Individual Healing Attempt with IgY:

The individual healing attempt with IgY was started when nocturnal resting pain no longer allowed cohesive night-time sleep and morning weakness in closing a first (both sides) for a duration of about 1 hour no longer guaranteed the patient was fit for work.

There were no further disease symptoms and this was the first pain syndrome at all for the patient.

The IgY therapy was started with the effervescent powder preparation with a daily dose of 1 sachet (5 g of IgY preparation from Preparation example 2).

In the course of the first treatment week no alleviation of the symptoms occurred.

Only in the 2nd week was there a significant reduction in pain to about half the starting level, and only rarely waking up in the night due to resting pain.

This improvement lasted for about 3 weeks, until the pain increased again after an infection of the upper respiratory passages (bronchitis, maxillary sinusitis). Thereafter, an additional IgY therapy with enteric tablets (in a dose of 2×4 tablets; corresponds to 3 g of IgY preparation from Preparation Example 2) was started.

Under this combination a virtually complete elimination of the symptoms then occurred for the first time. The patient reported waking up in the morning without stiff fingers, full capacity of the radial lower arm muscles and absence of nocturnal pain.

Residual symptoms no longer existed daily, the residual symptoms essentially being a sensitivity of the elbow to impact. Performance sport (cross-country skiing) is possible without restriction if the therapy is continued.

Two blood samples were taken to analyse the immunological activity parameters, one before the start of treatment and one in the state of substantial absence of symptoms.

The invention claimed is:

1. A method for treating oral mucositis after radiotherapy and/or chemotherapy comprising the step of administering orally to a subject in need thereof, a pharmaceutical preparation comprising an efficacious amount of IgY antibodies or their fragments, wherein said IgY antibodies or their fragments are anti-lipopolysaccharide polyclonal antibodies obtained from egg yolk of hens immunized with Gram-negative bacteria.

2. The method according to claim 1, wherein the preparation comprises anti-lipopolysaccharide IgY antibodies obtained from egg yolk of immunized chickens.

3. The method according to claim 1, wherein the treatment is carried out by administering a daily dose of a formulation prepared for administration of 0.1-10.0 g.

4. The method according to claim 1, wherein the treatment is carried out by administering a daily dose of a formulation prepared for administration of 1.0-8.0 g.

5. The method according to claim 1, wherein the treatment is carried out by administering a daily dose of a formulation prepared for administration of 2.0-7.0 g.

6. The method according to claim 1, wherein the treatment is carried out by a daily administration for 4-14 weeks.

7. The method according to claim 1, characterized in that the oral mucositis after radiotherapy and/or chemotherapy is present in a patient further suffering from an idiopathic pain syndrome.

8. The method according to claim 1, wherein the oral mucositis after radiotherapy and/or chemotherapy is present in a patient with a defective biological barrier against bacterial endotoxin.

9. The method according to claim 1, wherein said IgY antibodies or their fragments represent at least 1.5 wt % based on the total weight of the preparation.

10. The method according to claim 1, wherein said IgY antibodies or their fragments represent at least 2.0 wt % based on the total weight of the preparation.

11. The method according to claim 1, wherein said IgY antibodies or their fragments represent at least 5.0 wt % based on the total weight of the preparation.

12. The method according to claim 1, wherein said IgY antibodies or their fragments represent 100% of the total antibody content of the preparation.

* * * * *